(12) United States Patent
Yu et al.

(10) Patent No.: US 8,921,424 B2
(45) Date of Patent: Dec. 30, 2014

(54) HISTONE DEACETYLASE INHIBITORS, PROCESS FOR PREPARATION AND USES THEREOF

(75) Inventors: Niefang Yu, Changsha (CN); Xiaoyu Liu, Taizhou (CN); Xiaodong Hu, Taizhou (CN)

(73) Assignees: Zhejiang Hisun Pharmaceutical Co. Ltd., Zhejiang (CN); Central South University, Hunan (CN)

( * ) Notice: Subject to any disclaimer, the term of this patent is extended or adjusted under 35 U.S.C. 154(b) by 1134 days.

(21) Appl. No.: 12/739,635

(22) PCT Filed: Oct. 27, 2008

(86) PCT No.: PCT/CN2008/001802
§ 371 (c)(1),
(2), (4) Date: Apr. 23, 2010

(87) PCT Pub. No.: WO2009/067856
PCT Pub. Date: Jun. 4, 2009

(65) Prior Publication Data
US 2011/0218221 A1    Sep. 8, 2011

(30) Foreign Application Priority Data

Oct. 26, 2007 (CN) .......................... 2007 1 0047464

(51) Int. Cl.
| | | |
|---|---|---|
| A61K 31/195 | (2006.01) | |
| A61K 31/192 | (2006.01) | |
| C07C 259/04 | (2006.01) | |
| C07C 323/63 | (2006.01) | |
| C07D 333/20 | (2006.01) | |
| C07D 213/53 | (2006.01) | |
| C07C 311/07 | (2006.01) | |
| C07C 275/42 | (2006.01) | |
| C07C 335/22 | (2006.01) | |
| C07C 259/06 | (2006.01) | |

(52) U.S. Cl.
CPC ............ *C07C 323/63* (2013.01); *C07D 333/20* (2013.01); *C07D 213/53* (2013.01); *C07C 311/07* (2013.01); *C07C 275/42* (2013.01); *C07C 335/22* (2013.01); *C07C 259/06* (2013.01)
USPC .......................................... 514/575; 562/621

(58) Field of Classification Search
USPC .......................................... 514/575; 562/621
See application file for complete search history.

(56) References Cited

U.S. PATENT DOCUMENTS 6,541,661 B1 * 4/2003 Delorme et al. .............. 560/318

* cited by examiner

*Primary Examiner* — Samantha Shterengarts
(74) *Attorney, Agent, or Firm* — Milstein Zhang & Wu LLC

(57) ABSTRACT

The present invention relates to compounds represented by formula (I) or composition comprising at least one of such compounds, which are inhibitors of histone deacetylase. The detailed description of these compounds is disclosed in the Description. These compounds and the composition comprising the same may be useful as medicaments for the treatment of proliferative disorders as well as other diseases involving, relating to or associated with enzymes having histone deacetylase (HDAC) activities.

24 Claims, No Drawings

HISTONE DEACETYLASE INHIBITORS, PROCESS FOR PREPARATION AND USES THEREOF

FIELD OF THE INVENTION

The present invention relates to novel histone deacetylase inhibitors (HDACs), process for the preparation and uses thereof.

BACKGROUND OF THE INVENTION

Abnormal expressions of genes are closely related to many human diseases, including malignant diseases, endocrine disturbance, immune system disorders, genetic and nervous system disorders, and neurodegenerative disease. The human genome is existed in the form of chromatin structure which is packaged in place by DNA, histones and non-histone proteins, and the chromatin structure plays an important role in determining whether a specific gene is expressive or not. In general, highly packed chromatin suppress transcription, while active expression occurs in those loosely areas of the chromatin.

Inside the nuclei of eukaryotic cells, a nucleosomal core particle is composed of a fragment of DNA (146 bp) wrapped around a histone octamer and the chromatin was formed by the four histone partners and the DNA wrapped around. Histone modifications play important roles in gene transcriptions, DNA replications and DNA repairs. These modifications include methylation, acetylation, phosphorylation of a histone. Among them, the dynamic acetylation level of a histone is catalytically maintained by a pair of enzymes named histone acetylases and histone deacetylases (HDAC). Recent studies revealed that small organic molecules could regulate the histone acetylation level by competitively inhibiting HDACs and thus may be useful in the treatment of carcinoma diseases, cardiac disorders and parasitic diseases, etc. HDACs are now promising targets for diverse drug discovery.

Several classes of HDAC inhibitors (HDACi) have been reported, including (1) short fatty acid, such as butylic acid and phenylbutylic acid; (2) hydroximates, e.g. suberoylanilide hydroxamic acid (SAHA) and trichostatin A (TSA); (3) Cyclic Tetrapetides with 2-amino-8-oxo-9,10-epoxy-decanoyl, such as trapoxin and HC-toxon; (4) Cyclic Tetrapetides without 2-amino-8-oxo-9,10-epoxy-decanoyl, e.g. Apicidin and FK228; (5) Benzamides, such as MS-275 (EP 0847992, US 2002/0103192, WO 02/26696, WO 01/70675, WO 01/18171). Among them, SAHA was approved by FDA and launched in 2006 as Vorinostat (Zolinza), for the treatment of Cutaneous T-cell Lymphoma (George S. Mack: Journal of the National Cancer Institute, 2006; 98(20): 1443-1444).

WO 01/38322 discloses a HDAC inhibitor represented by the following formula (A):

$$Cy\text{-}L^1\text{-}Ar\text{-}Y^1\text{-}C(O)\text{-}NH\text{-}Z \quad (A)$$

Wherein,

Cy is selected from a group consisting of cylcloalkyl, aryl, heteroaryl or heterocycloalkyl, each of them may be optionally substituted;

$L^1$ is $-(CH_2)_m-W-$, m=0-4;

W is $-C(O)NH-$ or $-S(O)_2NH-$;

Ar is a substituted aryl;

$Y^1$ is a saturated or unsaturated hydrocarbon chain with or without substituents;

Z is selected from phenylamino, pyridinyl, thiadiazoyl, and $-O-M$, where M is H or a pharmaceutical acceptable cation ion.

WO 02/22577 discloses a HDAC inhibitor represented by the following formula (B):

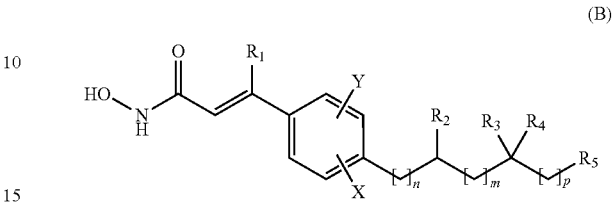

Wherein, $R_1$ is selected from a group consisting of H, halogen, and linear $C_1$-$C_6$ alkyl;

$R_2$ is selected from a group consisting of H, $C_1$-$C_{10}$ alkyl, $C_4$-$C_9$ cycloalkyl, $C_4$-$C_9$ heterocycloalkyl, $C_4$-$C_9$ heterocycloalkylalkyl, cycloalkylalkyl, aryl, heteroaryl, arylalkyl, heteroaryl alkyl and the like.

$R_3$ and $R_4$ are the same or different, and can be independently from each other selected from a group consisting of H, $C_1$-$C_6$ alkyl, acyl, acylamino; or $R_3$ and $R_4$, together with the carbon atom to which they all combine, form a C=O, C=S or C=$NR_8$; or $R_2$, together with the nitrogen to which $R_2$ combines, and $R_3$, together with the carbon to which $R_3$ combines, form a $C_4$-$C_9$ heterocycloalkyl, heteroaryl, fused-ring heteroaryl, non-aryl fused-ring heterocyclyl or mixed aryls and non-aryl fused-ring heterocyclyls;

$R_5$ is a H, $C_1$-$C_6$ alkyl, $C_4$-$C_9$ cycloalkyl, $C_4$-$C_9$ heterocycloalkyl, and the like;

n, m, p are the same or different, and can be independently from each other selected from 0-6; when n is 1-6, every carbon atom could be independently and optionally substituted by $R_3$ and/or $R_4$;

X and Y are the same or different and are independently from each other selected from a group consisting of H, halogen, $C_1$-$C_4$ alkyl, $NO_2$, $C(O)R_1$, $OR_9$, $SR_9$, CN and $NR_{10}R_{11}$;

US20060052599 discloses a HDAC inhibitor represented by the following formula (C):

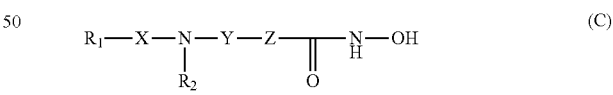

Wherein, $R_1$ is a lower alkyl, higher alkyl, lower alkenyl, lower or higher alkynyl, lower cycloalkyl, higher cycloalkyl, lower cyclalkyl-lower alkyl, higher cycloalkyl-lower alkyl, lower cycloalkenyl-lower alkyl, aryl-lower cyclo alkyl, lower alkoxy, acyl, aryl, aryl-lower-alkoxy, lower heteroalkyl, amino, heteroaryl, heterocyclyl, and the like;

$R_2$ is a H or lower alkyl; X is a aryl, heteroaryl, cycloaryl, etc; Y is a aryl or heteroaryl, etc; Z is a lower alkenyl, and the like.

U.S. Pat. No. 7,135,493 discloses another HDAC inhibitor shown by formula (D):

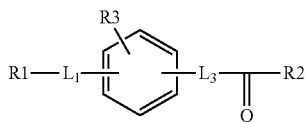

(D)

Wherein,

R1 is a N-containing heterocycloalkyl and it may be optionally substituted with one or more substituents;

R2 is a hydroxamate:

R3 is a H or a suitable substituent;

$L_1$ is $-(CH_2)_n-$, n: 0-6: each of these residual may be substituted by one or more substituent.

$L_3$ is a lower alkenyl.

However, there is still a need to provide further HDAC inhibitors that would be expected to be more effective, to have minimum side effects and more favourable pharmaceutical profiling.

SUMMARY OF THE INVENTION objects of this invention are to provide novel HDAC inhibitors, process for their preparation and uses of the same.

According to one object of this invention, novel HDAC inhibitors are represented by formula (I):

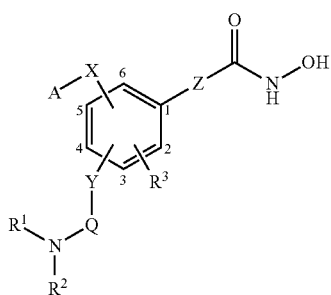

Formula (I)

wherein

A is selected from the group consisting of: H, $-NO_2$, $-NH_2$, alkyl, alkenyl, haloalkyl, haloalkenyl, heteroalkyl, alkoxy, alkoxyalkyl, alkenyloxy, alkynyloxy, alkylamino, aminoalkyl alkylaminocarbonyl, sulfonyl, alkylsulfonyl, alkylsulfinyl, aminosulfonyl, acyl, arylalkyl, cycloalkylaryl, heteroaryl and heterocyclyl, each of which may be optionally substituted by one or more substituent selected from the group consisting of halogen, $=O$, $-CF_3$, alkyl, alkenyl, alkynyl, hydroxyl, hydroxyalkyl, alkoxy, alkoxyalkyl;

X is selected from the group consisting of: methylene, $-O-$, $-S-$, $-NH-$, $-NR^7-$, $-CO-NH-$, $-CO-NR^7-$, $-NH-CO-$, $-NR^7-CO-$, $-SO_2NH-$, $-NH-SO_2-$, $-NH-CO-NH-$, $-NH-CS-NH-$, $-CO-NH-CO-NH-$, $-CS-NH-CO-NH-$, or a bond; when X is $-NH-$ or $-NR^7-$, A is neither aryl, heterocycloaryl, cycloalkenyl nor Heterocycloalkeny;

Y is selected from the group consisting of: $-O-$, $-S-$, $-NH-$ and $-S(O)-$;

X and Y are independently attached to the phenyl ring at its position $C_3$, $C_4$ or $C_5$;

Q is selected from a group consisting of $-(CR^8R^9)n-$, $-(CR^8R^9)n-X-(CR^{10}R^{11})m-$, $-Ar-X-(CR^{10}R^{11})m-$, $-(CR^8R^9)n-X-Ar-$, $-Cy-X-(CR^{10}R^{11})m-$, $-(CR^8R^9)n-X-Cy-$;

n, m is independently 1, 2, 3, 4, 5 or 6;

Z is C2-C6 alkenyl;

$R_1$ and $R^2$ are selected independently from a group consisting of H, alkyl, alkenyl, haloalkyl, haloalkenyl, haloalkynyl heteroalkyl, alkoxyl alkoxyalkyl, alkenoxy, alkynyloxy, amino, alkylamino, aminoalkyl, alkoxylcarbonyl, alkylaminocarbonyl, sulfonyl, alkylsulfonyl, alkylsulfinyl, aminosulfonyl and acyl, each of which may be optionally substituted by one or more substituent selected from the group consisting of halogen, $=O$, $=S$, $-CF_3$, $-OCF_3$, alkyl, alkenyl, alkynyl, hydroxyl, hydroxyalkyl, alkoxy, alkoxyalkyl; alkenoxy, alkynyloxy, amino, alkylamino;

$R^3$ is selected from the group consisting of H, nitro, amino, alkyl and halogen;

$R^7$ is H, alkyl, alkenyl, haloalkyl, haloalkenyl, cycloalkyl, heteroalkyl, hydroxyl, hydroxyalkyl, alkoxy, alkoxyalkyl, alkoxyaryl, alkenoxy, alkynoxy, cycloalkoxy, heterocycloalkoxy, amino, alkylamino, aminoalkyl, amide COOH, alkoxycarbonyl, alkylaminocarbonyl, sulfonyl, alkylsulfonyl, alkylsulfinyl, aminosulfonyl, and acyl, each of which may be optionally substituted by one or more substituent selected from halogen, $=O$, $=S$, $-CN$, $-NO_2$, $-CF_3$, $-OCF_3$, alkyl, alkenyl, alkynyl, haloalkyl, haloalkenyl, haloalkynyl, hydroxyl, hydroxyalkyl, alkoxy, alkoxyalkyl, alkenoxy, alkynoxy, amino, alkylamino, sulfonyl, alkylsulfonyl, aminosulfonyl, alkoxyalkyl, COOH, $-C(O)OR^4$, $-COR^5$, $-SH$, $-SR^6$, $-OR^6$ or acyl:

$R^5$, $R^6$, $R^8$, $R^9$, $R^{10}$ and $R^{11}$ are independently selected from a group consisting of: H, alkyl, alkenyl, haloalkyl, haloalkenyl, cycloalkyl, heteroalkyl, hydroxyl, hydroxyalkyl, alkoxy, alkoxyalkyl, alkoxyaryl, alkenoxy, alkynoxy, cycloalkoxy, heterocycloalkoxy, amino, alkylamino, aminoalkyl, amide, COOH, alkoxycarbonyl, alkylaminocarbonyl, sulfonyl, alkylsulfonyl, alkylsulfinyl, aminosulfonyl and acyl;

Ar is aryl, or heteroaryl, each of which may be optionally substituted by one or more substituent selected from halogen, $=O$, $-CF_3$, alkyl, alkenyl, alkynyl, hydroxy, hydroxyalkyl, alkoxy or alkoxyalkyl; Cy is cycloalkyl or heterocycloalkyl, each of which may be optionally substituted by one or more substituent selected from halogen, $=O$, $-CF_3$, alkyl, alkenyl, alkynyl, hydroxy, hydroxyalkyl, alkoxy or alkoxyalkyl; or pharmaceutically acceptable salts thereof.

In some embodiments, A is preferably selected from alkyl, alkenyl, acyl, aryl, heteroaryl, heterocycloalkyl or heterocycloalkenyl, each of which may be optionally substituted by one or more substituent;

X preferably selected from $-NH-$, $-NR^7-$, $-CO-NH-$, $-CO-NR^7-$, $-NH-CO-$, $-NR^7-CO-$, $-SO_2NH-$, $-NH-SO_2-$, $-NH-CO-NH-$, $-NH-CS-NH-$, $-CO-NH-CO-NH-$ and $-CS-NH-CO-NH-$; when X is $-NH-$ or $-NR^7$. A is neither aryl, heterocycloaryl, cycloalkenyl, nor Heterocycloalkeny;

Y is preferably $-O-$, $-S-$ or $-NH-$;

Q is preferably selected from $C_1$-$C_{10}$ alkyl and $C_1$-$C_{10}$ alkenyl;

$R^1$ and $R^2$ are selected independently from a group consisting of C1-C10 alkyl, C1-C10 alkenyl, C1-C10 heteroalkyl, haloalkyl, alkynyl, aryl, cycloalkyl, heterocycloalkyl, heteroaryl, C4-C9 heterocycloalkyl alkyl, cycloalkylalkyl, arylalkyl, and heteroarylalkyl;

Z is preferably $C_2$-$C_4$ alkenyl;

The above residuals may be further substituted.

In another embodiment, X is preferably $-NH-$, $-CONH-$, $-NR^7-$, or a covalent bond. $R^7$ is particularly preferred from methyl, ethyl, 2-hydroxy-ethyl, propyl, 3,3-dimethylbutyl, butyl, pentyl, allyl, phenyl, benzyl and 3,4,5-trimethoxybenzyl.

In another embodiment, most preferred Y is —S—,

In another embodiment, most preferred Z is —CH=CH—, the configuration of which is E.

In another embodiment, $R^1$ and $R^2$ are preferably selected from methyl, ethyl, 2-hydroxy-ethyl, propyl, 3,3-dimethylbutyl, butyl, pentyl, allyl, phenyl, benzyl and 3,4,5-trimethoxybenzyl.

In another embodiment, X is preferably attached to position $C_4$ and $C_5$ of the phenyl ring. Most preferably X is attached to the $C_5$ position.

In another embodiment, Y is preferably attached to position $C_4$ and $C_5$ of the phenyl ring. Most preferably Y is attached to the $C_4$ position.

In addition to the inventive compounds of Formula (I), the pharmaceutically acceptable salts of these compounds, the pharmaceutically acceptable prodrugs and pharmaceutically active metabolites of such compounds, and pharmaceutically acceptable salts of such metabolites are also covered by the present invention.

According to another object of the invention, provided are pharmaceutical compositions comprising at least one compound of the invention represented by the formula (I) or the corresponding salts, and pharmaceutically acceptable carrier.

According to another object of the invention, further provided is a use of the inventive compounds represented by the formula (I) or their pharmaceutically acceptable salts, or of the composition containing the aforesaid compounds or their pharmaceutically acceptable salts for preparation of the drug to be used as inhibitor of histone deacetylase.

According to another object of the invention, further provided is an use of the inventive compounds represented by the formula (I) or their pharmaceutically acceptable salts, or of the composition containing the aforesaid compounds or their pharmaceutically acceptable salts for preparation of the medicine to be used for treatment of a disorder caused by, associated with or accompanied by disruptions of cell proliferation and/or angiogenesis, through administration of a therapeutically effective amount of at least one of the compounds of formula (I) or their pharmaceutically acceptable salts, or through administration of a composition containing at least one of the compounds represented by formula (I) or their pharmaceutically acceptable salts.

The disorders caused by, associated with or accompanied by disruptions of cell proliferation and/or angiogenesis include, but not limited to, any one of the proliferative disorders (e.g. cancer); any one of the neurodegenerative diseases including Huntington's Disease, polyglutamine diseases, Parkinson's disease, Alzheimer's disease, seizures, striatonigral degeneration, progressive supranuclear palsy, torsion dystonia, spasmodic torticollis and dyskinesis, familial tremor, Gilles de la Tourette syndrome, diffuse Lewy body disease, Pick's disease, intracerebral haemorrhage, primary lateral sclerosis, spinal muscular atrophy, amyotrophic lateral sclerosis, hypertrophic interstitial polyneuropathy, retinitis pigmentosa, hereditary optic atrophy, hereditary spastic paraplegia, progressive ataxia and Shy-Drager syndrome; any one of the Metabolic diseases including Type 2 diabetes; any one of the degenerative diseases of the eye including glaucoma, age-related macular degeneration, macular myopic degeneration; any one of the inflammatory diseases and/or Immune system disorders including rheumatoid arthritis (RA), osteoarthritis, juvenile chronic arthritis, graft versus host disease, psoriasis, asthma, spondyloarthropathy, Crohn's disease, inflammatory bowel disease, colitis ulcerosa, alcoholic hepatitis, diabetes, Sjoegrens's syndrome, multiple sclerosis, ankylosing spondylitis, membranous glomerulopathy, discogenic pain, systemic lupus erythematosus, allergic contact dermatitis; any one of the diseases involving angiogenesis including cancer, psoriasis, rheumatoid arthritis; any one of the psychological disorders including bipolar disease, schizophrenia, depression and dementia; any one of the cardiovascular diseases including heart failure, restenosis, cardiac hypertrophy and arteriosclerosis; any one of the fibrotic diseases including liver fibrosis, lung fibrosis, cystic fibrosis and angiofibroma; any one of the infectious diseases including fungal infections, such as *Candida albicans*, in bacterial infections; any one of the viral infections, such as herpes simplex; any one of the protozoal infections, such as malaria, *leishmania* infection, *trypanosoma brucei* infection, toxoplasmosis and coccidiosis, and any one of the haematopoietic disorders including thalassemia, anemia and sickle cell anemia.

According to another object of the invention, further provided is a method of treating proliferation related diseases, in particularly cancer, by using a composition comprising at least one of the compounds represented by Formula (I) or their pharmaceutically acceptable salts, pharmaceutically acceptable carrier and diluent or excipient.

EMBODIMENTS

The present invention is described in more detail with the help of the following examples. However, it should be understood that these examples are used only to describe, but not to limit the scope of the present invention. Those experiments without being given specific experimental conditions in the examples could be performed under the normal conditions or according to those provided or suggested by the suppliers, unless otherwise stated. The ratio and the percentage data were given by weight, unless specified.

In the present application for invention, the preparation of N-hydroxyl cinnamic amide derivatives represented by the Formula (I) and their pharmaceutical applications are disclosed. These compounds may be used as, but not limited to, histone deacetylase inhibitors. These cinnamic amide derivatives may be used, as single active ingredient or together with other active ingredient(s), for preventing or treating disorders caused by, associated with or accompanied by disruptions of cell proliferation and/or angiogenesis either alone or together with pharmaceutically acceptable carrier and diluent or excipient. An example of such a disorder is cancer.

As used here, the term 'cancer' is a general term intended to encompass the vast number of conditions that are characterised by uncontrolled abnormal growth of cells.

The compounds represented by Formula (I) can be used for treating various cancers including, but not limited to, bone cancers including Ewing's sarcoma, osteosarcoma, chondrosarcoma and the like; brain and CNS tumours including acoustic neuroma, neuroblastomas, glioma and other brain tumours, spinal cord tumours, breast cancers, colorectal cancers, advanced colorectal adenocarcinomas; endocrine cancers including adenocortical carcinoma, pancreatic cancer, pituitary cancer, thyroid cancer, parathyroid cancer, thymus cancer, multiple endocrine neoplasma; gastrointestinal cancers including stomach cancer, esophageal cancer, small intestine cancer, liver cancer, extra hepatic bile duct cancer, gastrointestinal carcinoid tumour, gall bladder cancer; genitourinary cancers including testicular cancer, penile cancer, prostate cancer, gynaecological cancers including cervical cancer, ovarian cancer, vaginal cancer, uterus/endometrium cancer, vulva cancer, gestational trophoblastic cancer, fallopian tube cancer, uterine sarcoma, head and neck cancers including oral cavity cancer, lip cancer, salivary gland cancer, larynx cancer, hypopharynx cancer, orthopharynx cancer, nasal cancer, paranasal cancer, nasopharynx cancer; leukemias including childhood leukemia, acute lymphocytic leukemia, acute myeloid leukemia, chronic lymphocytic leukemia, chronic myeloid leukemia, hairy cell leukemia, acute promyelocytic leukemia, plasma cell leukemia, myelomas; haematological disorders including myelodysplastic syndromes, myeloproliferative disorders, aplastic anemia, fanconi anemia, waldenstroms macroglobulinemia; lung cancers including small cell lung cancer, non-small cell lung cancer, lymphomas including Hodgkin's disease, non-Hodgkin's lymphoma, cutaneous T-cell lymphoma, peripheral T-cell lymphoma, AIDS related Lymphoma; eye cancers including retinoblastoma, intraocular melanoma; skin cancers including melanoma, non-melanoma skin cancer, merkel cell cancer, soft tissue sarcomas such as childhood soft tissue sarcoma, adult soft tissue sarcoma, Kaposi's sarcoma; urinary system cancers including kidney cancer, wilms tumour, bladder cancer, urethral cancer, and transitional cell cancer.

The inventive compounds represented by Formula (I) of the present application are preferably used for treating breast cancer, lung cancer, ovarian cancer, prostate cancer, head and neck cancer, renal, gastic and brain cancer.

The inventive compounds represented by Formula (I) of the present application are more preferably used for treating cutaneous T-cell lymphoma (CTCL) and peripheral T-cell lymphoma.

The inventive compounds represented by Formula (I) of the present application are further more preferably used for treating solid tumours and hematologic malignancies.

The inventive compounds represented by Formula (I) of the present application or their pharmaceutical acceptable salts can also be used for treatment of disorders that have been implicated by or known to be mediated at least in part by HDAC activity, where HDAC activity is known to play a role in triggering disease onset, or whose symptoms are known or have been shown to be alleviated by HDAC inhibitors. Disorders of this type that are expected to be amenable to treatment by using the inventive compounds represented by Formula (I) of this application include but not limited to the following: the proliferative disorders (e.g. cancer); neurodegenerative diseases including Huntington's Disease, polyglutamine diseases, Parkinson's disease, Alzheimer's disease, seizures, striatonigral degeneration, progressive supranuclear palsy, torsion dystonia, spasmodic torticollis and dyskinesis, familial tremor, Gilles de la Tourette syndrome, diffuse Lewy body disease, Pick's disease, intracerebral haemorrhage, primary lateral sclerosis, spinal muscular atrophy, amyotrophic lateral sclerosis, hypertrophic interstitial polyneuropathy, retinitis pigmentosa, hereditary optic atrophy, hereditary spastic paraplegia, progressive ataxia and Shy-Drager syndrome; metabolic diseases including Type 2 diabetes; degenerative diseases of the eye including glaucoma, age-related macular degeneration, macular myopic degeneration, Inflammatory diseases and/or Immune system disorders including rheumatoid arthritis (RA), osteoarthritis, juvenile chronic arthritis, graft versus host disease, psoriasis, asthma, spondyloarthropathy. Crohn's disease, inflammatory bowel disease, colitis ulcerosa, alcoholic hepatitis, diabetes, Sjoegrens's syndrome, multiple sclerosis, ankylosing spondylitis, membranous glomerulopathy, discogenic pain, systemic lupus erythematosus, allergic contact dermatitis; disease involving angiogenesis including cancer, psoriasis, rheumatoid arthritis; psychological disorders including bipolar disease, schizophrenia, depression and dementia; cardiovascular diseases including heart failure, restenosis, cardiac hypertrophy and arteriosclerosis; fibrotic diseases including liver fibrosis, lung fibrosis, cystic fibrosis and angiofibroma; infectious diseases including fungal infections, such as *Candida albicans*, bacterial infections, viral infections, such as herpes simplex, protozoal infections, such as malaria, *leishmania* infection, *trypanosoma brucei* infection, toxoplasmosis, coccidiosis; and haematopoietic disorders including thalassemia, anemia and sickle cell anemia.

As used herein, the term 'unsubstituted' means that there is no substituent or that the only substituent is hydrogen. The term 'substituted' by one or more suitable substituent means that one or more hydrogens in the corresponding structure are replaced by (a) non-hydrogen substituent(s). The substituents are defined as following.

"Halogen" represents chlorine, fluorine, bromine or iodine.

"Alkyl" as a substituent or part of a substituent refers to a straight or branched aliphatic hydrocarbon residual, preferably a $C_1$-$C_{14}$ alkyl, more preferably $C_1$-$C_{10}$ alkyl, most preferably $C_1$-$C_6$, unless otherwise indicated. Examples of suitable straight and branched $C_1$-$C_6$ alkyl include, but not limited to, methyl, ethyl, n-propyl, 2-propyl, n-butyl, sec-butyl, t-butyl, hexyl, and the like.

"Alkylamino" includes both monoalkyl-amino and dialkyl-amino, unless otherwise specified. "Monoalkyl-amino" means a Alkyl-NH— residual, in which alkyl is as defined above. "Dialkyl-amino" means a (Alkyl)$_2$-N— residual, in which each alkyl may be the same or different and are each as defined above for alkyl. The alkyl residual mentioned here is preferably a $C_1$-$C_6$ alkyl. Examples of 'alkylamino' include, but not limited to, N-Methylamino, N-Ethylamino, N-Isopropylamino, N,N-(Diethyl)amino and the like.

"Aminoalkyl" means a —NH-Alkyl residual, in which alkyl is as defined above. Examples of 'Aminoalkyl' include, but not limited to, Aminoethyl, 1-Aminopropyl, 1-Aminopropyl, and the like.

"Arylamino" includes both monoaryl-amino and diaryl-amino, unless otherwise indicated. Monoaryl-amino means an aryl-NH—, in which aryl is as defined above; diaryl-amino means a (aryl)$_2$-N—, wherein each aryl may be the same or different and is as above herein for aryl.

"Acyl" means an alkyl-CO— or aryl-CO—, in which the alkyl group or aryl residual is as described above. Examples of acyl include, but not limited to, acetyl, propylacyl, isobutylacyl, benzoyl, and the like.

"Amide" refers to an alkyl-CONH— or aryl-CONH—, in which the alkyl or the aryl is as describe above. Examples of amide include, but not limited to, acetamido, propylamido, butylamido, isobutylamido, benzoylamino, and the like.

"Alkenyl" as a residual or part of a residual denotes an aliphatic hydrocarbon residual containing at least one carbon-carbon double bond and which may be straight or branched, preferably having 2-14 carbon atoms, more preferably 2-12 carbon atoms, most preferably 2-6 carbon atoms. In the normal chain, this residual may contain more than one double bonds and each of which may independently have an E or Z configuration. Exemplary alkenyl include, but are not limited to, ethenyl, propenyl.

"Straight Alkenyl" refers to a straight alkenyl containing at least one carbon-carbon double bond as defined above, The 'alkenyl' is preferably a $C_2$-$C_{12}$ alkenyl.

"Alkoxy" refers to an alkyl-O— in which alkyl is defined above. Preferably the alkoxy is a $C_1$-$C_6$ alkoxy. Examples of $C_1$-$C_6$ alkoxy include, but are not limited to, methoxy, ethoxy, n-proproxy, iso-proproxy, n-butoxy, iso-butoxy and the like.

"Alkenoxy" refers to an alkenyl-O— in which alkenyl is as defined above. Preferred alkenoxy is $C_1$-$C_6$ alkenoxy.

"Alkynyloxy" refers to an alkynyl-O— in which alkynyl is as defined above. Preferred alkynyloxy is $C_1$-$C_6$ alkynyloxy.

"Alkoxycarbonyl" refers to an alkyl-C(O)—O— in which alkyl is as defined above. The alkyl group is preferably a $C_1$-$C_6$ alkyl. Examples include, but not limited to, methoxycarbony, ethoxycarbonyl and the like.

"Alkylsulfinyl" means an alkyl-S(O)— in which alkyl is as defined above. The alkyl group is preferably a $C_1$-$C_6$ alkyl. Exemplary alkylsulfinyl includes, but not limited to, methylsulfinyl, ethylsulfinyl and the like.

"Alkylsulfonyl" refers to an alkyl-S(O)$_2$— in which alkyl is as defined above. The alkyl is preferably a $C_1$-$C_6$ alkyl. Examples include, but not limited to, methylsulfonyl, ethylsulfonyl and the like.

"Alkylaminocarbonyl" refers to an alkylamino-carbonyl in which alkylamino is as defined above.

"Cycloalkyl" refers to a saturated or partially saturated, monocyclic or fused or spiro polycyclic carbocycle, preferably containing from 3 to 9 carbons, Exemplary cycloalkyl includes, but not limited to, cyclopropyl, cyclobutyl, cyclopentyl, cyclohexyl and the like.

"Cycloalkylalkyl" means a cycloalkyl-alkyl- in which the cycloalkyl and alkyl moieties are as previously described. Monocycloalkylalkyl includes, but not limited to cyclopropylmethyl, cyclopentylmethyl, cyclohexylmethyl, cycloheptylmethyl and the like.

"Heterocycloalkyl" refers to a cycloalkyl containing at least one heteroatom in the ring system selected from nitrogen, sulphur, oxygen, preferably 1 to 3 heteroatoms in the ring. The ring is preferably 3 to 14 membered, more preferably 4 to 7 membered. Heterocycloalkyl includes, but not limited to, pyrrolidinyl, dihydropyrrolyl, tetrahydropyrrolyl, piperidyl, piperazyl, tetrahydrofuryl, tetrahydrothiofuranyl, tetrahydropyranyl, and the like.

"Heterocycloalkenyl" refers to a heterocycloalkyl as described above but containing at least one double bond.

"Heterocycloalkylalkyl" refers to a heterocycloalkyl-alkyl in which the heterocycloalkyl and alkyl moieties are as previously described. Exemplary heterocycloalkylalkyl include, in but not limited to, (2-tetrahydrofuryl)methyl, (2-tetrahydrothiofuranyl)methyl and the like.

"Heteroalkyl" refers to a straight- or branched-chain alkyl having at least one or more heteroatoms selected from S, O, and N. The Heteroalkyl has preferably 2 to 14 atoms in the chain heteroalkyl includes, but not limited to, those residuals derived from alkyl ether, alkyl ester alkylsulfides, secondary or tertiary alkylamines, alkyl sulfinic acid and the like.

"Aryl" as a residual or part of a residual denotes (i) An aromatic monocyclic or fused polycyclic, preferably aromatic carbocycle (ring structure having those ring atoms that are all carbon) having 5 to 12 carbon atoms. Examples of aryl include, but not limited to, phenyl, naphthyl; (ii) Those aryl which are attached to partially saturated carbocyclic, such as the bicyclic structure formed by fusing a phenyl with a $C_5$-$C_7$ cycloalkyl or with a C5-C7 cycloalkenyl, Exemplary aryl includes, but not limited to, tetrahydronaphthyl, indenyl or indanyl and the like. The aryl may be substituted by one or more substituents.

"Arylalkenyl" means an aryl-alkenyl- in which the aryl and alkenyl are as previously described. Exemplary arylalkenyl includes, but not limited to, phenylpropenyl and the like "Arylalkyl" means an aryl-alkyl- in which the aryl and alkyl moieties are as previously described. Exemplary arylalkyl include, but not limited to, benzyl, phenylethyl and 1-naphylmethyl and the like.

"Cycloalkenyl" means a non-aromatic monocyclic or multicyclic ring system containing at least one carbon-carbon double bond, and has preferably 5-10 carbon atoms per ring. Exemplary monocyclic cycloalkenyl rings include, but not limited to, cyclopentenyl, cyclohexenyl, cycloheptenyl and the like. Cycloalkenyl may be substituted by one or more substituents.

"Heteroaryl" refers to either monocyclic or fused multicyclic aromatic hereroccycliyl, preferably a 5-7 membered aromatic ring, having one or more heteroatoms selected from N, O or/and S as ring atoms. Typical hetreoaryl includes, but not limited to, for example those residuals derived from furan, thiophene, pyrrole, pyrazole, triazole, thiazole, pyridine, pyrazine, indole, benzimidazole, and the like.

"Heteroarylalkyl" means a heteroaryl-alkyl in which the heteroaryl and alkyl moieties are as previously described. Exemplary heteroarylalkyl includes, but not limited to, 2-furanylmethy, 3-furanylmethy, 2-pyridylmethyl, and the like.

It should be understood that included in the family of compounds of Formula (I) in this present invention are all their geometrical isomeric forms, including diastereoisomers, enantiomers, tautomers, and "E" or "Z" configurational isomer, or a mixture of E and Z configurational isomers. It should also be understood that all these isomeric forms can be separated by conventionally used physical and/or chemical methods for this purpose which are commonly known to those skilled in the art.

The inventive compounds of the Formula (I) should cover their possible single stereoisomers, racemates, enantiomers and/or mixtures of them.

Additionally, the inventive compounds of Formula (I) should cover, when in application, their possible solvated as well as un-solvated forms. Thus, each formula includes compounds having the indicated structure, including the hydrated as well as the non-hydrated forms.

In addition to the inventive compounds of the Formula (I), the HDAC inhibiting agents in various embodiment forms comprise pharmaceutically acceptable salts, prodrugs and active metabolites of such compounds, as well as the pharmaceutically acceptable salts of such metabolites.

The term "pharmaceutically acceptable salts" refers to those salts that can retain the desired biological activity of the above-identified compounds and are suitable for certain medical applications purposes, including pharmaceutically acceptable acid addition salts and base addition salts. Suitable pharmaceutically acceptable acid addition salts of compounds of Formula (I) may be prepared using an inorganic acid or from an organic acid. Such inorganic acids include hydrochloric acid, sulphuric acid, and phosphoric acid. Appropriate organic acids may be selected from aliphatic acids, cycloaliphatic acids, aromatic acids, heterocyclic carboxylic acids and sulfonic acids, and the like. Examples of such organic acids include, but not limited to, formic acid, acetic acid, propionic acid, succinic acid, glycolic acid, gluconic acid, lactic acid, malic acid, tartaric acid, glycine, arginine, citric acid, fumaric acid, alkyl sulfonic acid, arylsulfonic acid. Suitable pharmaceutically acceptable base addition salts of the inventive compounds of Formula (I) include metallic salts made from lithium, sodium, potassium, magnesium, calcium, aluminium, and zinc, and organic salts made from organic bases such as choline, diethanolamine, morpholine and the like.

"Prodrug" means a compound which is convertible in vivo by metabolic means (e.g. by hydrolysis, reduction or oxidation) to a compound of formula (I). For example, a compound of formula (I) containing a hydroxyl group can be reacted with acid to obtain the corresponding ester. And an ester prodrug of a compound of formula (I) containing a hydroxyl group may be convertible by hydrolysis in vivo to the parent molecule. Suitable esters of compounds of formula (I) containing a hydroxyl group, are, but not limited to, acetic acid, citric acid, tartaric acid, propionic acid, oxalic acid, salicylic acid, succinic acid, fumaric acid, maleic acid, Methyl-bis-β-hydroxynaphthoic acid, gentisic acid, Isethionic is acid, methanesulfonic acid, ethyl sulfonic acid, benzenesulfonic acid, p-toluenesulphonic acid, and the like.

Preferred HDAC inhibiting agents include those compounds having an $IC_{50}$ value of 100 μM or less.

Administration of compounds of Formula (I) to humans can be conducted by any of the accepted modes for enteral administration such as oral or rectal, or by parenteral administration such as subcutaneous, intramuscular, intravenous and intradermal routes. The active compounds may be administrated together with pharmaceutically acceptable carrier or diluent and in an amount sufficient to deliver to the patient a therapeutically effective dose.

The term "therapeutically effective amount" or "effective amount" is an amount sufficient to effectuate beneficial or desired results. An effective amount can be administered in one or more administrations. An effective amount is typically sufficient to palliate, ameliorate, stabilize, reverse, slow or delay the progression of the disease state.

The compounds of the present invention can be administered alone or in combination with one or more additional active ingredient(s) that are chemotherapeutic drugs or other HDAC inhibitor drugs, and/or in combination with other procedures, e.g. surgery or radiotherapy for the treatment of the disorder/diseases mentioned above. The compounds of the present invention can also be administered in the form of a pharmaceutical composition with a pharmaceutically acceptable carrier, diluent or excipient, depending on the desired mode of administration or therapeutic purposes.

Pharmaceutical compositions of this invention for parenteral injection comprise pharmaceutically acceptable sterile aqueous or non-aqueous solutions, dispersions, suspensions or emulsions as well as sterile powders for reconstitution into sterile injectable solutions or dispersions just prior to use.

If desired, and for more effective distribution, the compounds can be incorporated into slow release or targeted delivery systems such as polymer matrices, liposomes, and microspheres.

Solid dosage forms for oral administration include capsules, tablets, pills, powders, and granules. In such solid dosage forms, the active compound represented by Formula (I) is mixed with at least one inert, pharmaceutically acceptable excipient or carrier such as sodium citrate or dicalcium phosphate and/or a) fillers or extenders such as starches, lactose, sucrose, glucose, mannitol, and salicylic acid; b) binders such as, for example, carboxymethylcellulose, alginates, gelatin, polyvinylpyrrolidone, sucrose, and acacia; c) disintegrating agents such as agar-agar, calcium carbonate, potato or tapioca starch, alginic acid, certain silicates, and sodium carbonate; d) solution retarding agents such as paraffin; e) absorption accelerators such as quaternary ammonium compounds; f) wetting agents such as, for example, cetyl alcohol and glycerol monostearate; g) absorbents such as kaolin and bentonite clay; and h) lubricants such as talc, calcium stearate, magnesium stearate, solid polyethylene glycols, The solid dosage forms of tablets, dragees, capsules, pills, and granules can be prepared with coatings and shells.

The active compounds can also be in microencapsulated form, if appropriate, with one or more of the above-mentioned excipients.

Liquid dosage forms for oral administration include pharmaceutically acceptable emulsions, solutions, suspensions, and syrups. In addition to the active compounds, the liquid dosage forms may contain inert diluents commonly used in the art such as, for example, water or other solvents, solubilizing agents and emulsifiers such as ethyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and the like.

Besides inert diluents, the oral compositions can also include adjuvants such as wetting agents, emulsifying and suspending agents, sweetening, flavouring, and perfuming agents.

Suspensions may contain, in addition to the active compounds, suspending agents, for example, ethoxylated isostearyl alcohols, polyoxyethylene sorbitol and sorbitan esters, and the like.

Compositions for rectal or vaginal administration are preferably suppositories which can be prepared by mixing the compounds of this invention with suitable non-irritating excipients or carriers.

Dosage forms for topical administration of the compound of this invention include powders, patches, sprays, ointments and inhalants. The active compound is mixed under sterile conditions with a pharmaceutically acceptable carrier and any needed preservatives, buffers, or propellants which may be required.

A preferred dosage could be in a range of from about 0.01 to 300 mg per kilogram of body weight per day. A more preferred dosage could be in the range of from 0.1 to 80 mg per kilogram of body weight per day. A suitable dose can be administered in multiple sub-doses per day.

As discussed above, the compounds of the present invention can inhibit histone deacetylases. The enzymatic inhibitory activities of the compounds represented by Formula (I) against a histone deacetylase can be measured using known methods (J. Biol. chem., 1990; 265:171-74; Science, 1996; 272:408)

The compounds represented by Formula (I) of the present invention can be used especially to treat cancers including, but not limited to, breast cancer, lung cancer, ovarian cancer, prostate cancer, head and neck cancer, renal, gastic and brain cancer. In addition, the compounds of this invention can be also used to treat diseases involving angiogenesis including hematologic malignancies, psoriasis.

Additionally, the compounds of the present invention may be useful for treating neurodegenerative diseases, and inflammatory diseases and/or immune system disorders.

The particular compounds of the present invention may be prepared using the reaction routes and synthesis processes as described below. The indicated starting materials are readily available. More ever, the artisan can, when making reference to the teachings of the present application and in combination with the basic knowledge of chemistry, recognize that the chemical reactions described may be readily adapted by using appropriate starting materials, so as to prepare a number of other target compounds represented by Formula (I). For examples, for synthesis of those non-exemplified compounds, what need to be done by a skilled in the art is to change the starting materials to that matching the new targeted compound and, if necessary, to conduct minor modification to the reaction conditions, then the new targeted compound could be obtained in the light of the teachings of the present application in combination of the common knowledge in the art.

Reagents required for synthesizing the target inventive compounds may be obtained or prepared from their corresponding raw materials, according to teachings of the synthesis routes and processes as discussed below, in combination with the techniques known in the art.

The synthesis of some specific inventive compounds is exemplified in detail in the following examples. However it is known to a skilled person in the art that the other non-exemplified compounds could also be prepared similarly by making reference to the synthesis examples, sometime some modification/changes to the exemplified reaction parameters might be necessary, for example, using another protective group for certain reaction sensitive substituent, choosing a more suitable reagent or modifying the reaction conditions to certain extent, etc. A list of the suitable protective groups for organic synthesis could be found from the book "T. W. Greene: Protective Groups in organic Synthesis, John Wiley & Sons, 1981"; Similar knowledge is familiar with to the skilled in the art, known from other books or handbooks.

In the examples described below, unless otherwise indicated, all temperatures in the following description are in degrees Celsius, unless indicated otherwise.

Various starting materials and other reagents were purchased from commercial suppliers, including but not limited to, Aldrich Chemical Company or Lancaster Synthesis Ltd., and the commercially available starting materials and other reagents can be used without further purification, unless otherwise indicated Glassware was oven-dried and/or heat-dried. Analytical thin-layer chromatography was performed on glass-backed silica gel 60 F 254 plates (E Merck (0.25 mm)) and eluted with the appropriate solvent ratios (v/v). The reactions were assayed by TLC and terminated when the starting materials are consumed out.

Work-ups were typically done by doubling the reaction volume with the reaction solvent and then extracting with the indicated solutions using 25% by volume of the extraction volume (unless otherwise indicated) by three times. Product solutions were dried over anhydrous sodium sulfate prior to filtration, and evaporation of the solvents was conducted under reduced pressure on a rotary evaporator and noted when solvents removed in vacuo. Flash column chromatography was used to purify the target product (J. Org. Chem., 1978, 43:2923-2925)

$^1$HNMR spectra were recorded on a Bruker spectrometer operating at 300 MHz or 400 MHz for $^1$H NMR. Chemical shifts are expressed in ppm, using chloroform (7.25 ppm) or DMSO-$d_6$ (0.00 ppm) as the reference standard, or otherwise as indicated. Other NMR solvents could also be used as needed. When peak multiplicities are reported, the following abbreviations are used: s=singlet, d=doublet, t=triplet, q=quartet, m=multiplet, br=broadened, dd=doublet of doublets, dt=doublet of triplets. Coupling constants, when given, are reported in Hertz.

Mass spectra were obtained using LC/MS either in ESI or APCI. All melting points are uncorrected.

The following examples are given to illustrate how the inventive compounds could be synthesized and should not to be construed as being limitations thereto. Additional compounds, other than those described below, may be prepared using the following described reaction scheme and process and, if necessary, together with some minor and appropriate variations or modifications thereof.

Scheme I illustrates the procedure used for preparing compounds of Formula (I), wherein z=—CH=CH—, and X and Y are attached to $C_5$- and $C_4$-position respectively; for example, when $R_3$ is hydrogen and X=NH, the corresponding compounds of Formula (I) can be prepared by analogous method illustrated in Scheme (I) by condensation of trans-3-nitro-4-chloro-cinnamic acid with appropriate amide derivatives ($R^1R^2$N-Q-YH), followed by esterification, reduction and condensation with aldehydes, and finally obtaining the end product through reaction with hydroxylamine or N-alkyl hydroxylamine ($NH_2OH$) in the presence of a suitable base, such as sodium methoxide.

Scheme 1

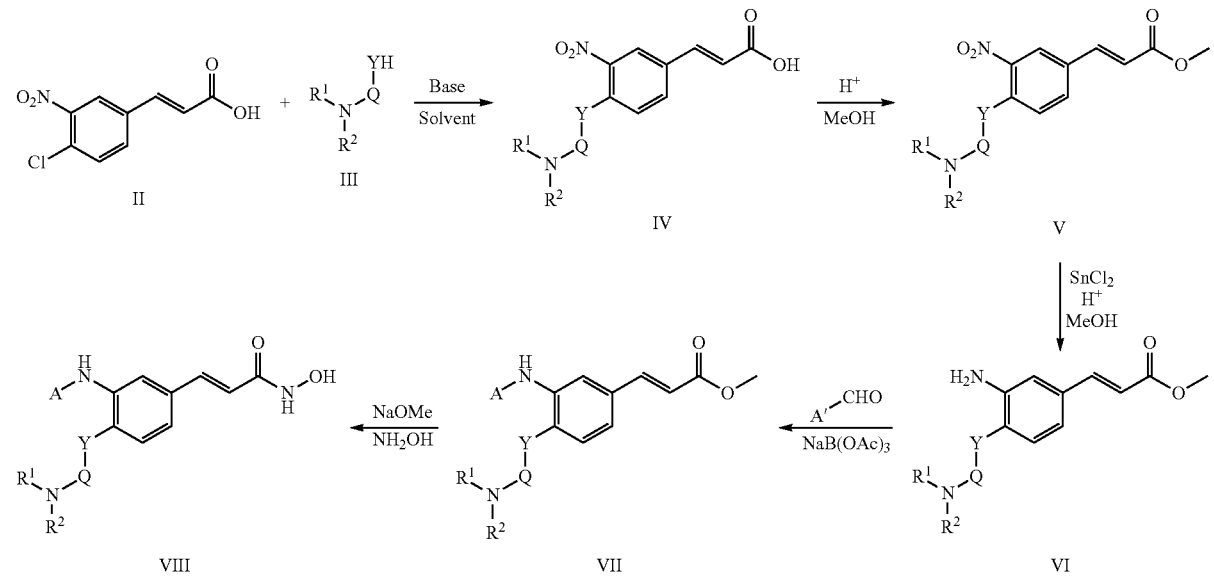

Y = O, S

Specifically, when z=—CH=CH—, $R_3$ is hydrogen, X,Y are attached to $C_5$- and $C_4$-position respectively, the hydroxamate compounds (VIII) represented by Formula (I) can be synthesized by using appropriate starting materials shown in the synthetic route shown in Scheme I. Reaction of trans-4-chloro-3-nitrocinnamic acid (II) with a suitable amine derivatives (with a mercapto or a hydroxyl as a substituent) (III) in the present of a base (e.g. triethylamine) in an appropriate solvent (e.g. dioxane, tetrahydrogenfuran), giving (IV). Treatment of (IV) in methanol under acid catalysis (e.g. sulfuric acid) resulted in esterification providing (V). The nitro group of (V) can be reduced into amino by appropriate reducing agent (e.g. tin (II) chloride) and the resulting amino compound (VI) was coupled reductively with an agent A'-CHO to give key intermediate (VII). The hydroxamate compounds (VIII) were obtained from methyl ester (VII) by a known synthesis method.

The compounds represented by Formula (I) may also be synthesized by using appropriate starting materials shown in Scheme 2. The compound (VI) prepared according to Scheme 1 was treated with an appropriate acid (A'-COOH), or an appropriate acyl chloride (A'-COOCl), or an appropriate sulfonyl chloride (A'-$SO_2$Cl) under suitable catalyst, giving compound (IX). Compounds (VI) reacts with an appropriate A'-NCO or A'-NCS, giving compounds (XI). Compounds (VI) can also react with appropriate acyl-isocyanates A'-CO—NCO or acyl-isothiocyanates A'-CO—NCS in a suitable solvent, giving compounds (XIII). The final target compounds (X), (XII), and (XIV) were obtained after treating the corresponding key intermediates (IX), (XI) and (XIII) with appropriate hydroxylamine under catalysis of sodium methoxide.

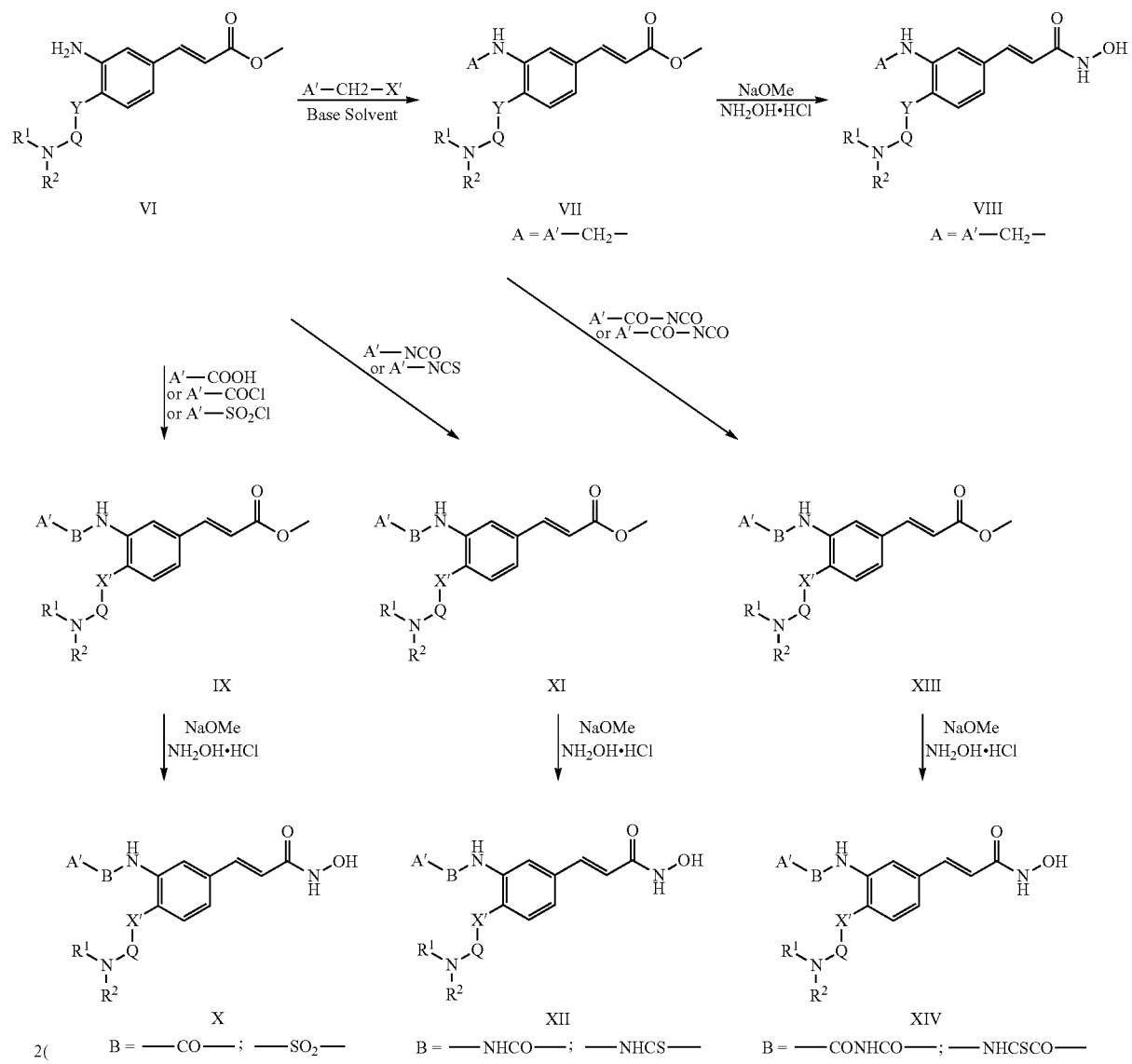

The following preparation examples are given to enable those skilled in the art to more clearly understand and to practice the technical solutions of the present invention. They should not be considered as limiting the scopes of the disclosure and of the claimable protection, but merely as being illustrative and representative thereof.

Example 1

Preparation of 3-(4-(2-(Diethylamino)ethylthio)-3-(3-phenylpropylamino)phenyl)-N-hydroxy-acrylamide (1)

Step 1

4-Chloro-3-nitro-cinnamic acid (1.14 g, 5.0 mmol) was suspended in methanol (70 mL), KOH (4.21 g, 75 mmol) and diethylamino-ethanethiol (in excess) were added respectively the suspension. The resulted mixture was stirred at a temperature of −10° C.-50° C. for 1-24 hours. Adjust the PH to 3.0-9.0 using concentrated hydrochloric acid at −10° C.-50° C. Removing the solvent under reduced pressure at 20-80° C. (water bath). To the residue, added is 100 mL water under stirring for dissolving it and adjusted the pH value to 1-5. Collecting and washing the yellow precipitates, washing it twice using cold water and then the product is obtained: 3-(4-(2-(diethylamino)ethylthio)-3-nitrophenyl)acrylic acid (Yield: quantitative). TLC: Rf=0.2 (DCM:MeOH=9:1). HPLC: 96.6%; $t_R$=7.25 min (LC/PDA: Diamonsil C18 5μ 150×4.6 mm, flow rate: 1.0 mL/min, grade: 10-100% B, 20 minutes; mobile phase A: water; mobile phase B: acetonitrile; UV254); MP: 229.4° C.-230.1° C. IR (cm$^{-1}$): 3364, 1680, 1603, 1465, 936. $^1$HNMR (400 MHz, CDCl$_3$) δ: 10.77 (1H, s), 8.51 (1H, d, J=1.6 Hz), 8.07 (1H, d, J=1.6 Hz), 7.88 (1H, d, J=8.8 Hz), 7.69 (1H, d, J=16 Hz), 6.73 (1H, d, J=16 Hz), 3.59 (2H, t, J=4 Hz); 3.15-3.27 (6H, br); 1.22 (6H, t, J=7.2 Hz). MS (m/z): 324 (MH)$^+$.

Step 2

3-(4-(2-(Diethylamino)ethylthio)-3-nitrophenyl)acrylic acid (1.74 g, 5.4 mmol) was suspended in methanol (25 mL) under stirring. To this solution, concentrated sulfuric acid (1.0 mL) was added. The resulted solution was heated to reflux for 19 hours. Cooling it to room temperature and the solvent was removed under reduced pressure. 100 ml water was added to dissolve the resulted residue. Cooling it with an ice-bath and adjusting the pH value to 9.0 using ammonia under stirring. (E)-methyl 3-(4-(2-(diethylamino)ethylthio)-3-nitrophenyl) acrylate was obtained as yellow solid. TLC: Rf=0.75 (DCM: MeOH=9:1); MP: 57.4° C.-59.1° C. HPLC: 92.0%; $t_R$=9.74 min (LC/PDA: Diamonsil C18 5μ 150×4.6 mm, flow rate: 1.0 mL/min, grade: 10-100% B, 20 minutes: mobile phase A: water; mobile phase B: acetonitrile; UV254); IR (cm$^{-1}$): 2967, 2926, 1720, 1639, 1604, 918. $^1$HNMR (400 MHz, CDCl$_3$) δ: 8.36 (1H, s), 7.70 (1H, d, J=1.6 Hz), 7.69 (1H, d, J=16 Hz), 7.50 (1H, d, J=8 Hz), 7.27 (1H, s), 6.51 (1H, d, J=16 Hz), 3.83 (3H, s), 3.12 (2H, t, J=8 Hz); 2.83 (2H, t, J=8 Hz); 2.64 (4H, q, J=7.2 Hz), 1.07 (6H, t, J=7.2 Hz). MS (m/z): 339 (MH)$^+$.

Step 3

(E)-Methyl 3-(4-(2-(diethylamino)ethylthio)-3-nitrophenyl)acrylate (736 mg, 2.2 mmol) was suspended in 15 mL solution of glacial acetic acid-Methanol. Under stirring, Tin Chloride (4.9 g, 21.7 mmol) was added and the resulted solution was heated to 0-100° C. for 0.5-5.0 hours. Cooling it then to room temperature. Removing the solvent under reduced pressure. Slowly add saturated sodium carbonate (20 mL) and dichloromethane (20 mL) to the residue with thoroughly stirring for 10-120 min. The organic layer was separated and dried with MgSO$_4$. Removing off MgSO$_4$ and the filtrate was concentrated into an oil. The product was purified through chromatography. 496.3 mg of (E)-methyl 3-(3-amino-4-(2-(diethylamino)ethylthio)-phenyl)acrylate was obtained. Yield: 73.9%. TLC: 0.31 (DCM:MeOH=9:1). MP: 153.2° C.-154.6° C. HPLC: 98.5%; $t_R$=7.82 min (LC/PDA: Diamonsil C18 5μ 150×4.6 mm, flow rate 1.0 mL/min, grade: 10-100% B, 12 minutes; mobile phase A: H2O; mobile phase B: acetonitrile; UV254). $^1$HNMR (400 MHz, CDCl$_3$) δ: 7.56 (1H, d, J=16 Hz), 7.39 (1H, d, J=8 Hz), 7.28 (1H, s), 6.87 (1H, dd, J=8 Hz and 16 Hz), 6.39 (1H, d, J=16 Hz), 4.51 (2H, s), 3.81 (3H, s), 3.05 (6H, m), 1.29 (6H, t, J=7.2 Hz); MS (m/z): 309 (MH)$^+$.

Step 4

250 mg (0.62 mmol) of (E)-methyl 3-(3-amino-4-(2-(diethylamino)ethylthio)-phenyl)acrylate was suspended in acetonitrile (5 mL) and to this solution, 3-phenylpropionaldehyde (108 mg, 0.8 mmol) was added under stirring. Then, sodium triacetoxyborohydride (636 mg, 3 mmol) was added and the resulted mixture was stirred at room temperature for 3-60 hours. Water and ethyl acetate was added after removing the solvent—acetonitrile. Collecting organic layers and drying it, 229 mg of (E)-methyl 3-(4-(2-(diethylamino)ethylthio)-3-(3-phenylpropylamino)phenyl)acrylate was obtained in a form of an oily product after being purified by chromatography. Yield: 86.6%. TLC: Rf=0.6 (DCM: MeOH=9:1). HPLC: 91%; tR=9.90 min (LC/PDA: Diamonsil C18.5μ 150×4.6 mm, flow rate 1.0 mL/min, grade: 10-100% B, 18 minutes; mobile phase A: H2O; mobile phase B: acetonitrile; UV254). MS (m/z): 427 (MH)$^+$.

Step 5

Under stirring, sodium methoxide (30% in methanol; 2.72 g, 15.1 mmol) was added to a methanol (1.6 mL) solution of (E)-methyl 3-(4-(2-(diethylamino)ethylthio)-3-(3-phenylpropylamino)phenyl)acrylate (229 mg, 0.54 mmol) and hydroxylamino hydrochloride (750 mg, 10.8 mmol). The resulted mixture was kept at room temperature for 5-50 min, then a pre-cooled HCl-MeOH solution was added and pH was adjusted to 7. Solvent was removed under reduced pressure. The product was purified by chromatography. 5 mg of (E)-3-(4-(2-(diethylamino)ethylthio)-3-(3-phenylpropylamino)-phenyl)-N-hydroxy-acrylamide (I) was obtained. Yield: 2%. TLC: Rf=0.23 (DCM:MeOH=9:1); HPLC: 93.1%; $t_R$=8.16 min (LC/PDA: Diamonsil C18 5μ 150×4.6 mm, flow rate 1.0 mL/min, grade: 10-100% B, 20 minutes; mobile phase A: H2O; mobile phase B: acetonitrile; UV254); $^1$HNMR (400 MHz, DMSO-δ6) δ: 10.68 (1H, s), 9.00 (1H, s), 7.17-7.37 (6H, m), 6.77 (1H, d, J=8.0 Hz), 6.72 (1H, s), 6.40 (1H, d, J=16.0 Hz), 5.45 (1H, br), 3.20 (2H, q, J=6.4 Hz), 2.86 (2H, br), 2.69 (3H, t, 8.0 Hz), 1.90 (2H, m, 3.2 Hz), 0.92 (6H, br). MS (m/z): 428 (MH)$^+$.

Examples 2-17

Wide variety of compounds represented by Formula (I) could be prepared according to the procedures described in Example 1 by using appropriate starting materials. The compounds of Examples 2-17 are only some typical representatives (Table 1).

TABLE 1

| Example | Structure | Name | m/z[MH]+ |
|---|---|---|---|
| 1 | 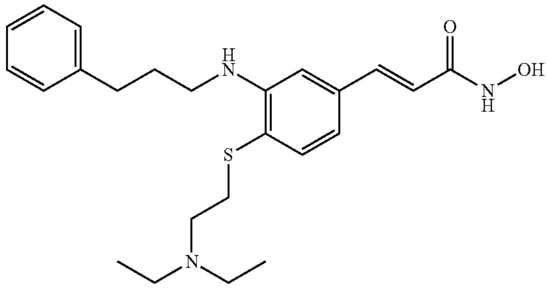 [SMILES: CCN(CC)CCSc1ccc(/C=C/C(=O)NO)cc1NCCCc1ccccc1] | 3-(4-(2-(diethylamino)ethylthio)-3-(3-phenylpropylamino)phenyl)-N-hydroxy-acrylamide | 428 |
| 2 | 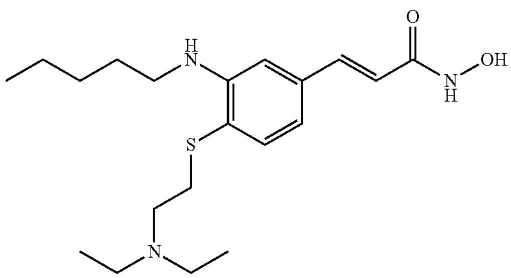 [SMILES: CCCCCNc1cc(/C=C/C(=O)NO)ccc1SCCN(CC)CC] | 3-(4-(2-(diethylamino)ethylthio)-3-(pentylamino)phenyl)-N-hydroxy-acrylamide | 380 |
| 3 | 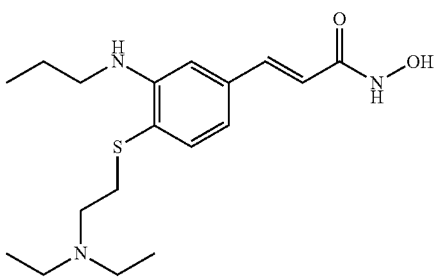 [SMILES: CCCNc1cc(/C=C/C(=O)NO)ccc1SCCN(CC)CC] | 3-(4-(2-(diethylamino)ethylthio)-3-(propylamino)phenyl)-N-hydroxy-acrylamide | 352 |
| 4 | 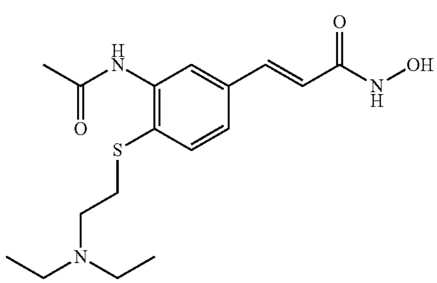 [SMILES: CCN(CC)CCSc1ccc(/C=C/C(=O)NO)cc1NC(C)=O] | 3-(3-acetamido-4-(2-diethylamino)ethylthio)phenyl)-N-hydroxy-acrylamide | 352 |
| 5 | 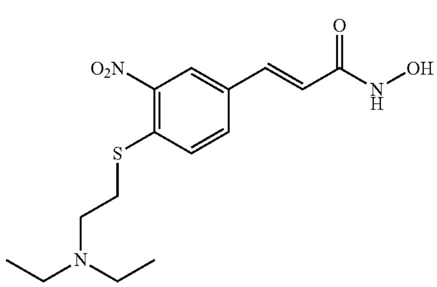 [SMILES: CCN(CC)CCSc1ccc(/C=C/C(=O)NO)cc1[N+](=O)[O-]] | 3-(4-(2-(diethylamino)ethylthio)-3-nitrophenyl)-N-hydroxy-acrylamide | 340 |

TABLE 1-continued

| Example | Structure | Name | m/z[MH]+ |
|---|---|---|---|
| 6 | 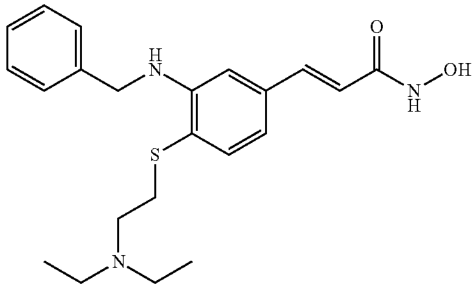 [SMILES: CCN(CC)CCSc1ccc(/C=C/C(=O)NO)cc1NCc1ccccc1] | 3-(3-(benzylamino)-4-(2-(di-ethylamino)ethylthio)phenyl)-N-hydroxy-acrylamide | 400 |
| 7 | 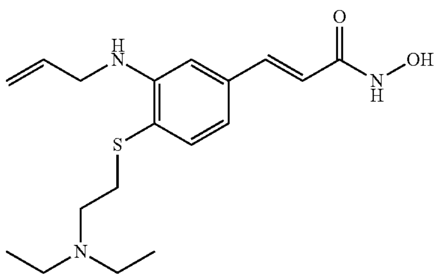 [SMILES: C=CCNc1cc(/C=C/C(=O)NO)ccc1SCCN(CC)CC] | 3-(3-(allylamino)-4-(2-(di-ethylamino)ethylthio)phenyl)-N-hydroxy-acrylamide | 350 |
| 8 | 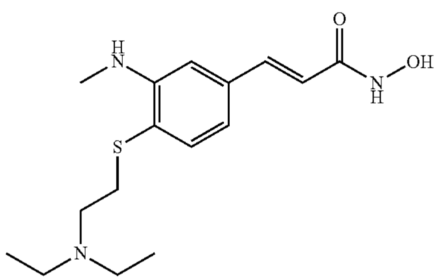 [SMILES: CCN(CC)CCSc1ccc(/C=C/C(=O)NO)cc1NC] | 3-(4-(2-(diethylamino)ethylthio)-3-(methylamino)phenyl)-N-hydroxy-acrylamide | 324 |
| 9 | 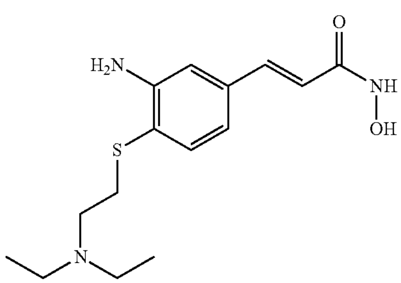 [SMILES: CCN(CC)CCSc1ccc(/C=C/C(=O)NO)cc1N] | 3-(3-amino-4-(2-(diethylamino)ethylthio)phenyl)-N-hydroxy-acrylamide | 310 |
| 10 | 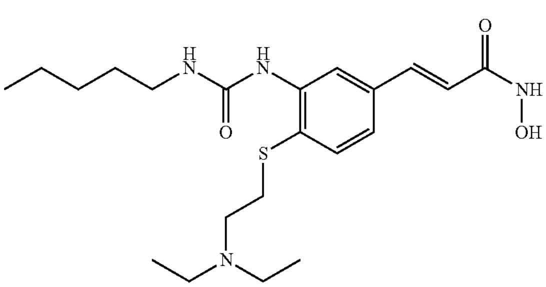 [SMILES: CCCCCNC(=O)Nc1cc(/C=C/C(=O)NO)ccc1SCCN(CC)CC] | 3-(4-(2-(diethylamino)ethylthio)-3-(3-pentylureido)phenyl)-N-hydroxy-acrylamide | 423 |

TABLE 1-continued

| Example | Structure | Name | m/z[MH]+ |
|---|---|---|---|
| 11 | 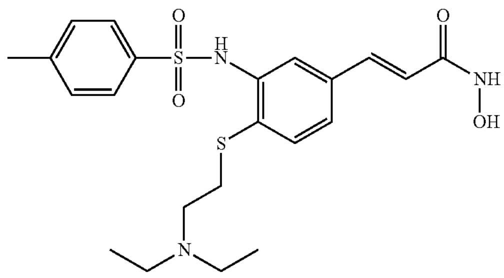 [SMILES: CCN(CC)CCSc1ccc(/C=C/C(=O)NO)cc1NS(=O)(=O)c1ccc(C)cc1] | 3-(4-(2-(diethylamino)ethylthio)-3-(4-methylphenylsulfonamido)phenyl)-N-hydroxy-acrylamide | 465 |
| 12 | 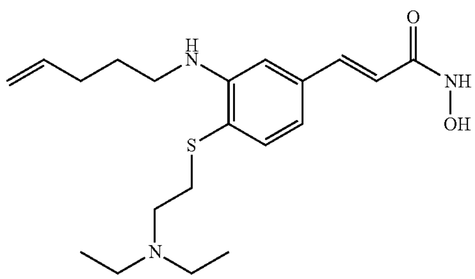 [SMILES: C=CCCCNc1cc(/C=C/C(=O)NO)ccc1SCCN(CC)CC] | 3-(4-(2-(diethylamino)ethylthio)-3-(pent-4-enylamino)phenyl)-N-hydroxy-acrylamide | 378 |
| 13 | 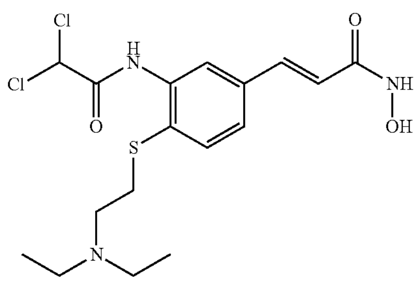 [SMILES: CCN(CC)CCSc1ccc(/C=C/C(=O)NO)cc1NC(=O)C(Cl)Cl] | 3-(3-(2,2-dichloroacetamido)-4-(2-(diethylamino)ethylthio)phenyl)-N-hydroxy-acrylamide | 421 |
| 14 | 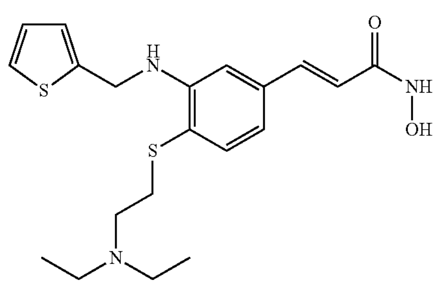 [SMILES: CCN(CC)CCSc1ccc(/C=C/C(=O)NO)cc1NCc1cccs1] | 3-(4-(2-(diethylamino)ethylthio)-3-(thiophen-2-ylmethylamino)phenyl)-N-hydroxy-acrylamide | 406 |
| 15 | 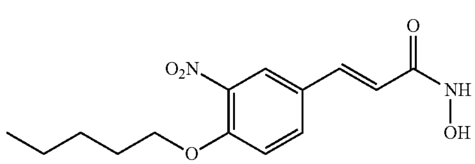 [SMILES: CCCCCOc1ccc(/C=C/C(=O)NO)cc1[N+](=O)[O-]] | 3-(4-(2-(diethylamino)ethylthio)-3-nitrophenyl)-N-hydroxy-acrylamide | 295 |
| 16 | 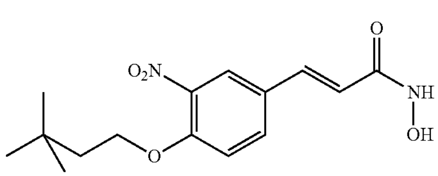 [SMILES: CC(C)(C)CCOc1ccc(/C=C/C(=O)NO)cc1[N+](=O)[O-]] | 3-(4-(3,3-dimethylbutoxy)-3-nitrophenyl)-N-hydroxy-acrylamide | 309 |

TABLE 1-continued

| Example | Structure | Name | m/z[MH]+ |
|---|---|---|---|
| 17 | 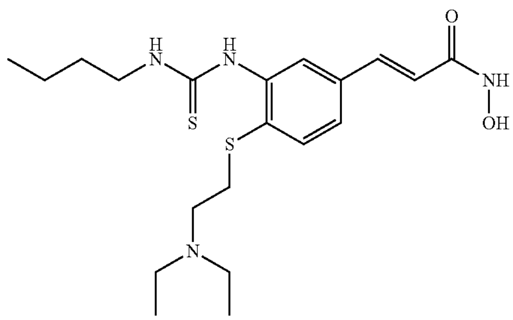 [SMILES: CCCCNC(=S)Nc1cc(/C=C/C(=O)NO)ccc1SCCN(CC)CC] | 3-(3-(3-butylthioureido)-4-(2-(diethylamino)ethylthio)phenyl)-N-hydroxy-acrylamide | 426 |

Examples 18-35

By methods analogous to those disclosed above and by choosing appropriate starting materials to be used in the following synthesis, a wide variety of compounds of Formula (I) could be prepared, including, but not limited to, those typical examples (Examples 18-35) listed in Table 2:

TABLE 2

Other Representative Compounds of Invention 18, 19, 20, 21, 22, 23, 24

TABLE 2-continued
Other Representative Compounds of Invention
25 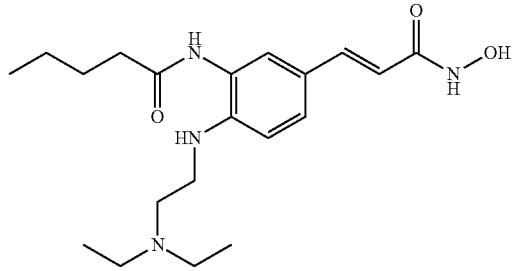 [SMILES: CCCCC(=O)Nc1cc(/C=C/C(=O)NO)ccc1NCCN(CC)CC]
26 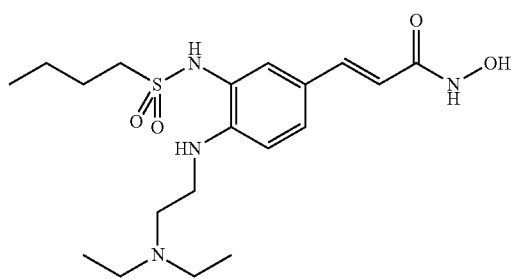 [SMILES: CCCCS(=O)(=O)Nc1cc(/C=C/C(=O)NO)ccc1NCCN(CC)CC]
27 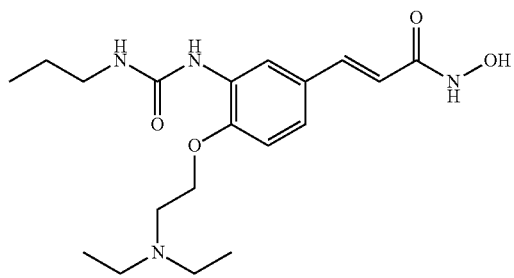 [SMILES: CCCNC(=O)Nc1cc(/C=C/C(=O)NO)ccc1OCCN(CC)CC]
28 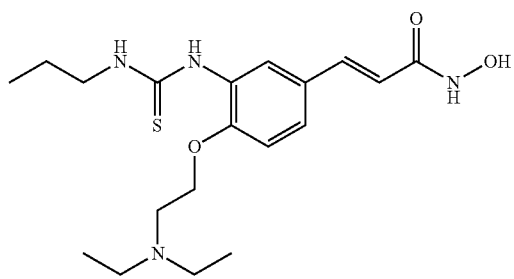 [SMILES: CCCNC(=S)Nc1cc(/C=C/C(=O)NO)ccc1OCCN(CC)CC]
29 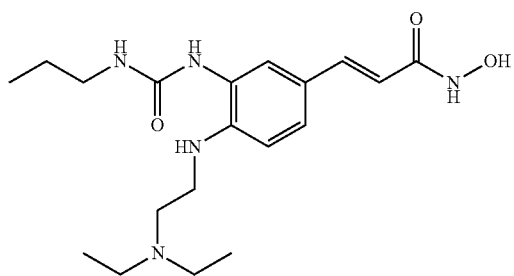
30 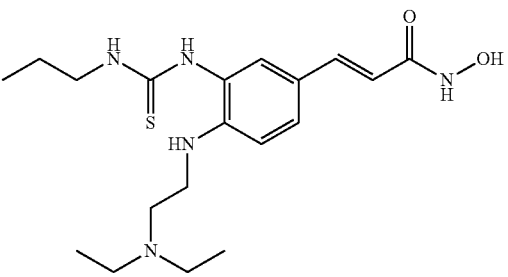 [SMILES: CCCNC(=O)Nc1cc(/C=C/C(=O)NO)ccc1NCCN(CC)CC]
31 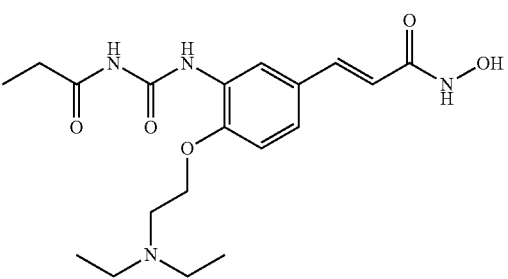 [SMILES: CCC(=O)NC(=O)Nc1cc(/C=C/C(=O)NO)ccc1OCCN(CC)CC]
32 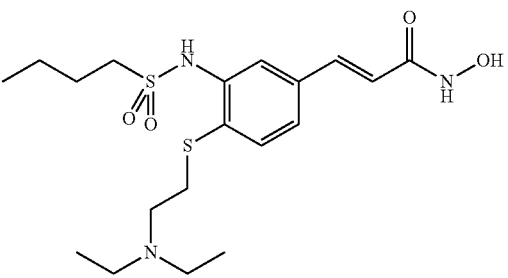 [SMILES: CCCCS(=O)(=O)Nc1cc(/C=C/C(=O)NO)ccc1SCCN(CC)CC]
33 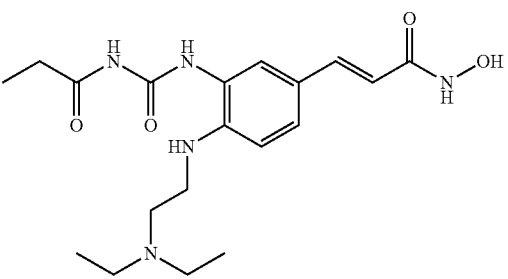 [SMILES: CCC(=O)NC(=O)Nc1cc(/C=C/C(=O)NO)ccc1NCCN(CC)CC]
34 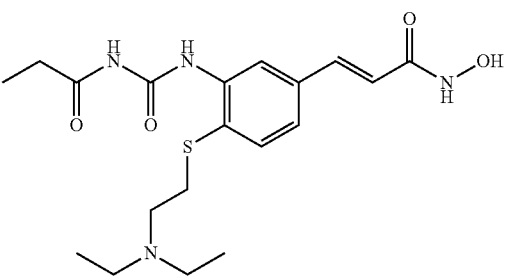

TABLE 2-continued

Other Representative Compounds of Invention

35

[Chemical structure: A compound with a pentyloxy group, a benzene ring with a thioether linked to a diethylaminoethyl group, and an acrylohydroxamic acid group]

Example 36

Biological Test and Efficacy Assays

In Vitro HDACi Assay for Determination of $IC_{50}$ Values

The BIOMOL fluorescent-based HDAC activity assay has been applied in In vitro HDACi assay for determination of $IC_{50}$ values of the compounds of this invention. The assay has been carried out in white 96 well formats according to the BIOMOL's method. In order to optimize the experiment conditions and optimal, the exact concentration range of the Deacetylated Standard (biomol, KI-142) that will vary depending on the flurimeter model, the gain setting and the exact excitation and emission wavelengths used. We recommend diluting some of the standard to a relatively low concentration with Assay Buffer (an appropriate series of Deacetylated Standard dilutions from 20 µM to 0.3125 µM), and Assay Buffer as a time zero to a set of wells on the microtiter plate. Experimental to samples (five dilute groups: 100 µM, 20 µM, 4 µM, 0.8 µM, 0.16 µM) should be compared to a time zero (sample for which Developer is added immediately after mixing the HDAC with substrate), a negative control (no enzyme) and a positive control (SAHA, 4 µM), the reaction mixture composed of assay buffer (containing 50 mM Tris pH 8.0, 137 mM NaCl, 2.7 mM KCl, 1 mM MgCl2, 1 mg/ml BSA), testing compounds or a drug as a positive control, an appropriate concentration of HDAC1 (600 nM) or HDAC8 (500 nM), 200 µM Flur de lys generic substrate for HDAC1 enzyme and 200 µM for HDAC8. The reaction mixture was incubated at room temperature for 2 hours. Flur de lys Developer was added and the reaction was incubated for 10 min. Briefly, deacetylation of the substrate sensitizes to the developer, which then generates a fluorophore. The fluorophore is excited with 360 nm light and the emitted light (460 nm) is detected on a fluorometric plate reader (Molecular Device Ultra Microplate detection system, MD Group Ltd).

The analytical software, Prism 4.0 (GraphPad Software Inc) has been used to generate $IC_{50}$ from a series of data. The HDAC enzyme inhibition results of representative compounds are shown in Table 3. These results indicated that the compounds of this invention possess potent and selective HDAC inhibitory activities.

Cell-Based Proliferation Assay for Determination of $GI_{50}$ Values

A rapid multiwell plate assay using Sulforhodamine B (SRB) protein stain was adopted to evaluate the growth inhibitory effects of the compounds of the present invention. The screening panel of cancer cell lines includes Colo205 and HCT116 colon cancer cells, MDA-MB231 and MDA-MB435 chest cancer cells, A549 lung cancer cells, and Chinese hamster ovary cell line CHO, which were obtained from ATCC.

The cell line Colo205 is grown in RPMI 1640 medium containing 2 mM L-glutamine, 5% fetal bovine serum, and 1.0 mM sodium pyruvic acid. Cell lines A549 and MDA-MB231 are grown in RPMI 1640 medium containing 2 mM L-glutamine and 5% fetal bovine serum. The cell line MDA-MB435 is grown in DMEM medium containing 2 mM L-glutamine and 5% fetal bovine serum. The cell lines HCT 116 is grown in IMEM medium containing 2 mM L-glutamine and 5% fetal bovine serum. The CHO cell line, used as a normal control on toxicity, is grown in a special medium for cell line. For a typical screening experiment, A549 and Colo205 cells are inoculated into 96-well microtiter plates, with 100 µL per well, and 2000 and 5000 cells per well respectively for either cell line. MDA-MB435, HCT116, MDA-MB231 and CHO cells are also inoculated into 96-well microtiter plates, with 6000 cells per well. After cell inoculation, the microtiter plates are incubated at 37° C., 5% CO2, and 100% relative humidity for 24 hr in order to make cells adhere to well wall.

After 24 h incubation or time zero for drug addition, with each cell line 50 µl of cold 50% (w/v) TCA is added to wells used for control to fix cells in situ. Also at time zero, cells in other wells are treated with 100 µl of compound of different concentrations for 24 hr, 48 hr, and 72 hr respectively, with varying final compound concentration (0.1 µM, 1 µM, 5 µM 10 µM). For each treatment duration at each compound concentration, there are triplicate wells, as well as an array of control wells including a blank control well (cell culture medium only, no cells), a no-compound control well (adding same volume of cell culture medium but no compound), a positive control well (treated with Suberoylanilide hydroxamic acid (SAHA)), and normal cell well control (CHO cells). Following the addition of compounds, cell plates are incubated for 24 h, 48 h or 72 h per treatment group at 37° C., 5% CO2, and 100% relative humidity. The Treatment is then terminated by addition of cold TCA and incubation of 1 hr at 4° C. The supernatant is discarded, and all wells are washed five times with de-ioned water and air dried. Then each well is added with 100 µl sulforhodamine B (SRB) solution (0.4% (w/v) made in 1% acetic acid) and cell plates are incubated for 20-30 minutes at room temperature. After staining, unbound dye is removed by washing five times with 1% acetic acid and the plates are air dried. Bound stain is subsequently solubilized with 10 mM (200 µL) Tris base with the help of 5 min platform vibration or pipetting up and down, and the absorbance is read on an automated plate reader (M5 detection system, MD Group Ltd.) at a wavelength of 565 nm (calibrated zero reading of blank control at wavelength of 690 nm). The analytical software, XL-fit has been used to generate $GI_{50}$ from a series of data thus obtained.

The results of representative compounds are shown in Table 3. These results indicated that the compounds of this invention possess potent and selective toxicology to human tumour cell lines, especial colon cancer.

TABLE 3

Deacetylase and Tumour Cell Inhibitory Activity of some Inventive Compounds

| No | IC$_{50}$ (nM) HDACs | IC$_{50}$ (nM) HDAC6 | GI$_{50}$ (μM) MDAMB435 | GI$_{50}$ (μM) HL-60 | GI$_{50}$ (μM) Colo205 | GI$_{50}$ (μM) HCT116 | GI$_{50}$ (μM) SKOV-3 | GI$_{50}$ (μM) BXPC-3 |
|---|---|---|---|---|---|---|---|---|
| 1 | 98 | 627 | 3.33 | 3.52 | 5.68 | 0.78 | 4.57 | 15.00 |
| 2 | 21 | 578 | 3.10 | 3.51 | 4.23 | 3.99 | 5.46 | 6.89 |
| 3 | 19 | 653 | 2.6 | 1.98 | 2.95 | 3.65 | 2.58 | 14.52 |
| 4 | >100 | 357 | — | — | — | — | — | — |
| 5 | 86 | 313 | 3.56 | 1.63 | 2.00 | 2.02 | 0.70 | 95.43 |
| 6 | 35 | 275 | 1.95 | 1.32 | 2.28 | 0.78 | 2.81 | 4.33 |
| 7 | >100 | 350 | — | — | — | — | — | — |
| 8 | 95 | 800 | 16.55 | 15.23 | 10.63 | 13.86 | 15.64 | 15.98 |
| 9 | >100 | 295 | — | — | — | — | — | — |
| 10 | 55 | 200 | 10.23 | 15.69 | 17.56 | 18.23 | 16.85 | 19.86 |
| 11 | >100 | 247 | — | — | — | — | — | — |
| 12 | >100 | 310 | — | — | — | — | — | — |
| 13 | 96 | 313 | 5.96 | 4.31 | 5.63 | 2.56 | 3.82 | 97.68 |
| SB939 | 18 | 488 | 2.65 | 0.645 | 2.409 | 1.355 | 5.25 | 6.78 |
| SAHA | 58 | 100 | 4.10 | 2.00 | 3.15 | 1.52 | 3.56 | 5.68 |

Measure of Microsomal Stability and Clearance with Compounds of this Invention

Verapamil (positive control) and compound solution, both at 10 mM, are diluted 200 fold. There are six reaction time points in the experiment (0 min, 5 min, 15 min, 30 min, 45 min, and 60 min), and triplicate samples are used for each data point. There are controls for time zero and negative drug effect (negative control containing no incubation buffer or enzyme). For each compound or Verapamil sample, there are also samples treated with compound or Verapamil at concentrations of no positive effect (at 5 μM and 2.5 μM, respectively). Diluted positive control (Verapamil) and compound solution are mixed with pre-heated (37° C.) incubation buffer (100 mM potassium phosphate buffer, NADPH regeneration system solution B, NAPDH regeneration system solution A, HLM/MLM in Milli-Q ultrapure water), and incubated at 37° C. for 10 min. 100 μL of stop solution mixture is (containing 80% acetonitrile, and 20% DMSO, both of HPLC grade) is dispensed into wells of separate sampling plates into each well. At each reaction time point (0 min, 5 min, 15 min, 30 min, 45 min, and 60 min) 50 μL of reaction solution is taken from wells in the incubation plate and transferred to its corresponding well in the sampling plate, and mixed by pipetting up and down with stop solution already added there. The sampling plates are then covered, placed on ice, and centrifuged at 2,000 rpm at 4° C. for 15 min. 100 μL supernatant is then taken from each well to LC/MS analysis (or stored at 4° C. in refrigerator until analysis).

Data analysis: % remaining of compound is calculated by area of each time point with respect to time 0% remaining against time (min) curve is plotted using the first-phase exponential decay equation $y=y_0e(-kT)$ on the Prism 4.0. Results are shown in the format of TOP, K, $t_{1/2}$ (min), R2 value and % remaining against time curve.

These results indicated that the compounds of this invention are stable in mouse and human live microsomes.

TABLE 4

| Compound | HDAC enzyme inhibition activity IC$_{50}$ (μM) | GI$_{50}$ (μM) MDAMB435 | HL-60 | Colo205 | HCT116 | SKOV-3 | BXPC-3 | MDAMB231 | $t_{1/2}$(h) |
|---|---|---|---|---|---|---|---|---|---|
| 1 | 98 | 3.33 | 3.52 | 5.68 | 0.78 | 4.57 | 3.33 | 3.49 | 1.4 |
| 2 | 21 | 3.10 | 3.51 | 4.23 | 3.99 | 5.46 | 3.10 | 3.50 | 1.8 |
| 3 | 19 | 2.6 | 1.98 | 2.95 | 3.65 | 2.58 | 2.6 | 2.98 | 1.8 |
| 4 | 86 | 3.56 | 1.63 | 2.00 | 2.02 | 0.70 | 3.56 | 4.63 | 1.6 |
| 5 | 35 | 1.95 | 1.32 | 2.28 | 0.78 | 2.81 | 1.95 | 1.92 | 2.2 |
| 6 | 96 | 5.96 | 4.31 | 5.63 | 2.56 | 3.82 | 5.96 | 4.39 | 2.5 |
| SB939 | 18 | 2.65 | 0.645 | 2.409 | 1.35 | 5.25 | 6.78 | 2.35 | 1.9 |
| SAHA | 58 | 4.10 | 2.00 | 3.15 | 1.52 | 3.56 | 5.68 | 5.10 | 1.6 |

Histone H3 Acetylation Assay

A hallmark of histone deacetylase (HDAC) inhibition is the increase in the acetylation level of histones. Histone acetylation, including H3, H4 and H2A can be detected by immunoblotting (western-blot). Appropriate number of Colo205 cells were seeded in a medium, cultivated for 24 h and subsequently treated with 0.1, 1.5 and 10 μM HDAC inhibitory agents and a positive control. After 24 h, cells were harvested and lysed according to the instruction from Sigma Mammalian Cell Lysis Kit. The protein concentration was quantified using BCA method (Sigma Pte Ltd). The protein lysate was separated using 4-12% bis-tris SDS-PAGE gel (Invitrogen Pte Ltd) and was transferred onto PVDF membrane (BioRad Pte Ltd). The membrane was probed using primary antibody (Upstate Pte Ltd) which is specific for acetylated H3, H4 and/or H2A. The detection antibody, goat rabbit antibody conjugated with HRP was used according to the to manufacture's instruction (Pierce Pte Ltd). After removing the detection antibody from the membrane, an enhanced chemo-luminescent substrate for detection of HRP (Pierce Pte Ltd) was added onto the membrane. After removing the substrate, the membrane was exposed to an X-ray film (Kodak) for from one second to 20 minutes. The X-ray film was developed using the X-ray film processor. The density of each band observable on the developed film could be qualitatively analyzed using UVP Bio-imaging software (UVP, Inc, Upland, Calif.). The values were then normalized against the density of actin in the corresponding samples to obtain the expression of the protein.

These data demonstrate that compounds of this invention inhibit histone deacetylases, thereby resulting in the accumulation of acetylated histones.

In Vivo Anti-Neoplastic (or Anti-Tumour) Effect of HDAC Inhibiting Agents

The efficacy of the selected compounds of the invention can then be determined using in vivo animal (mouse) xenograft studies. The animal xenograft model is one of the most commonly used in vivo cancer models for studying the pharmaceutically effective dosage, administration route, frequency and interval.

Athymic nude mice (Female, 5-6 week old, BALB/c, nu/nu, approximately 18-20 g body weight) are obtained from Vital River. The animals are kept on a 12 h light/dark cycle (0700-1900); food and water are provided ad libitum. All in vivo experiments are carried out in a specific pathogen-free facility (22° C.). The human cancer allogeneic transplant model in athymic nude mice is constructed using xenograft cell lines colon cancer cell line colo205, breast cancer cell line MDA-MB435, and lung cancer cell line A549, all obtained from ATCC. Cultured cells are removed from culture plate wall by digestion, collected and suspended in cell culture medium containing no FBS, at a concentration of 5×10⁶/0.2 ml, and brought to animal facility on ice. is 0.2 ml cell suspension is given to mice via rear left auxilliary subcutaneous scapular injection, using Size 6 needle. Animals are measured every 2-3 days on the size of tumor formation. After two weeks, those tumors that have been well grown without leak are removed from animals under sterile condition, split into several small fractions (2-3 mm in diameter), and injected s.c. into the rear left auxilliary subcutaneous scapular of animals. After three generations, mice bearing tumors either too big or too small are removed from the study, while those bearing tumor of 100 mm³ in size ( ) are randomized into five treatment groups, including three compound groups (receiving 4, 12, 20 mg/kg of test compound, respectively), positive control group (receiving SAHA, 4 mg/kg) and vehicle control group. There are 8 mice per compound group as well as in the positive control group. There 16 mice in the vehicle control group. All animals are given weekly injections i.p. continuously for 4 weeks. While the animas being treated, body weight of the animal and size of the tumor are measured every 3 days, with mortality also recorded. All animals are sacrificed 24 hr after the final injection. Tumors are removed, weighed, and measured. The curves for tumor volume growth and mice body weight growth are plotted. Tumor-inhibition rate, mortality, as well as relative tumor proliferationrate T/C (%) are calculated. T/C (%)=TRTV/CRTV*100%, whereas TRTV refers to treatment group RTV and CRTV refers to vehicle group RTV. RTV, or relative tumor volumes, is ( ) defined as the ratio between tumor volume immediately after treatment (Vt) and tumor volume immediately prior to treatment (V0).

These results indicated that the compounds of this present have T/C %≤50%. Significant differences in tumor growth rate were determined by analysis of variance (Table 5).

TABLE 5

Anticancer Activities in the Xenagrafe Model

| | | Compounds 2 | SAHA | SB939 |
|---|---|---|---|---|
| Compound 2 in Deverse Xenafrage Models T/C(%) | HCT-116 | 31% (300,14) | >60% (80,15) | 30% (30,14) |
| | COLO-205 | 42% (200,12) | >60% (80,12) | 55% (30,12) |
| | MDA-MB-435 | >60% (200,15) | >60% (80,15) | 58% (30,15) |
| | PC-3 | 43% (200,15) | 37% (80,15) | >60% (30,15) |
| | SKOV-3 | 45% (200,21) | >60% (80,20) | >60% (30,20) |
| | HL-60 | 40% (200,15) | 45% (80,10) | 51% (30,10) |

Note:
Data in blanket indicated Dose and time (mg/kg, days);
T/C(%) < 60%, effective;
administration, i.p;
Vehicle, Ethanol:Castor oil:Water = 1:1:12

All of the papers mentioned in the present application are incorporated as part of contents of the present invention by reference in the same way as they are referred to separately. It should also be understood that a skilled person in the art may, having got to know the teachings of the present application, make various modifications and/or changes to the present invention without departure from the spirits of the invention, and all these equivalents/variants of the present invention will fall within the protection scope as defined in the Claims.

What is claimed is:

1. A compound of the formula (I):

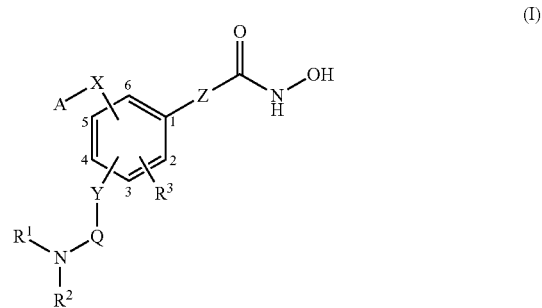

wherein,

A is selected from the group consisting of: H, —NO₂, —NH₂, alkyl, alkenyl, haloalkyl, haloalkenyl, heteroalkyl, alkoxy, alkoxyalkyl, alkenyloxy, alkynyloxy, alkylamino, aminoalkyl, alkylaminocarbonyl, sulfonyl, alkylsulfonyl, alkylsulfinyl, aminosulfonyl, acyl, arylalkyl, cycloalkylaryl, heteroaryl, and heterocycloalkyl, each of which is optionally substituted by one or more substituent selected from the group consisting of halogen, =O, —$CF_3$, alkyl, alkenyl, alkynyl, hydroxyl, hydroxyalkyl, alkoxy, alkoxyalkyl;

X is a covalent bond or a residual selected from the group consisting of methylene, —O—, —S—, —NH—, —$NR^7$—, —CO—NH—, —CO—$NR^7$—, —NH—CO—, —$NR^7$—CO—, —$SO_2$NH—, —NH—$SO_2$—, —NH—CO—NH—, —NH—CS—NH—, —CO—NH—CO—NH— and —CS—NH—CO—NH—; when X is —NH— or —$NR^7$—, A is neither aryl, heterocycloaryl, cycloalkenyl nor Heterocycloakeny;

Y is selected from the group consisting of —O—, —S—, —NH— and —S(O)—;

X and Y are respectively attached to the phenyl ring position $C_3$, $C_4$ and or $C_5$;

Q is selected from a group consisting of —$(CR^8R^9)$n-, —$(CR^8R^9)$n-X—$(CR^{10}R^{11})$m-, —Ar—X—$(CR^{10}R^{11})$m-, —$(CR^8R^9)$n-X—Ar—, —Cy—X—$(CR^{10}R^{11})$m- and —$(CR^8R^9)$n-X—Cy—;

n and m are independently 1, 2, 3, 4, 5 or 6;

Z is a $C_2$-$C_6$ alkenyl;

$R^1$ and $R^2$ are same or different and are selected independently from a group consisting of H, alkyl, alkenyl, haloalkyl, haloalkynyl, heteroalkyl, alkoxy, alkoxyalkyl, alkenoxy, alkynyloxy, amino, alkylamino, aminoalkyl, alkoxylcarbonyl, alkylaminocarbonyl, sulfonyl, alkylsulfonyl, alkylsulfinyl, aminosulfonyl and acyl, each of which is optionally substituted by one or more substituent selected from the group consisting of halogen, =O, =S, —$CF_3$, —$OCF_3$, alkyl, alkenyl, alkynyl, hydroxyl, hydroxyalkyl, alkoxy, alkoxyalkyl; alkenoxy, alkynyloxy, amino, alkylamino;

$R^3$ is selected from the group consisting of H, nitro, amino, alkyl and halogen;

$R^7$ is H, alkyl alkenyl, haloalkyl, haloalkenyl, cycloalkyl, heteroalkyl, hydroxyl, hydroxyalkyl, alkoxy, alkoxyalkyl, alkoxyaryl, alkenoxy, alkynoxy, cycloalkoxy, heterocycloalkoxy, amino, alkylamino, aminoalkyl, amide, COOH, alkoxycarbonyl, alkylaminocarbonyl, sulfonyl, alkylsulfonyl, alkylsulfinyl, aminosulfonyl, or acyl; each of which is optionally substituted by one or more substituent selected from halogen, =O, =S, —CN, —$NO_2$, —$CF_3$, —$OCF_3$, alkyl, alkenyl, alkynyl, haloalkyl, haloalkenyl, haloalkynyl, hydroxyl, hydroxyalkyl, alkoxy, alkoxyalkyl, alkenoxy, alkynoxy, amino, alkylamino, sulfonyl, alkylsulfonyl, aminosulfonyl, —COOH, —$C(O)OR^4$, —$COR^5$, —SH, —$SR^6$, —$OR^6$ and acyl;

$R^5$, $R^6$, $R^8$, $R^9$, $R^{10}$ and $R^{11}$ are independently from each other selected from a group consisting of H, alkyl, alkenyl, haloalkyl, haloalkenyl, cycloalkyl, heteroalkyl, hydroxyl, hydroxyalkyl, alkoxy, alkoxyalkyl, alkoxyaryl, alkenoxy, alkynoxy, cycloalkoxy, heterocycloalkoxy, amino, alkylamino, aminoalkyl, amide, COOH, alkoxycarbonyl, alkylaminocarbonyl, sulfonyl, alkylsulfonyl, alkylsulfinyl, aminosulfonyl and acyl;

Ar is aryl or heteroaryl, each of which is optionally substituted by one or more substituent selected from halogen, —$CF_3$, alkyl, alkenyl, alkynyl, hydroxy, hydroxyalkyl, alkoxy or alkoxyalkyl;

Cy is cycloalkyl or heterocycloalkyl, each of which is optionally substituted by one or more substituent selected from halogen, =O, —$CF_3$, alkyl, alkenyl, alkynyl, hydroxy, hydroxyalkyl, alkoxy or alkoxyalkyl;

or pharmaceutically acceptable salts, or prodrug thereof.

2. A compound of claim 1, wherein A is selected from a group consisting of alkyl, alkenyl, acyl, each of which is optionally substituted by one or more substituent selected from halogen, =O, —$CF_3$, alkyl, alkenyl, alkynyl, hydroxy, hydroxyalkyl, alkoxy and alkoxyalkyl.

3. A compound of claim 1, wherein X is selected from a group consisting of: —NH—, —$NR^7$—, —CO—NH—, —CO—$NR^7$—, —NH—CO—, —$NR^7$—CO—, —$SO_2$NH—, —NH—$SO_2$—, —NH—CO—NH—, —NH—CS—NH—, —CO—NH—CO—NH—, and —CS—NH—CO—NH—; when X is —NH— or —$NR^7$, A is neither aryl, heteroaryl, cycloalkenyl, nor heterocycloalkenyl.

4. A compound of claim 1, wherein X is —NH—, —CONH—, —$NR^7$—, or a covalent bond, wherein $R^7$ is selected from a group consisting of methyl, ethyl, 2-hydroxyethyl, propyl, 3,3-dimethylbutyl, butyl, pentyl, and allyl.

5. A compound of claim 1, where A-X is selected from a group consisting of —$NH_2$, —$NO_2$, —F, —Cl, methylamino, propylamino, isopropylamino, n-butylamino, iso-butylamino, pentylamino, hexyllamino, 2-(diethylamino)-ethylamino, 3-hydroxypropylamino, 3-(methoxy)propylamino, 3-isopropoxypropylamino, 2,2-(dimethyl)-propylamino, 3-(dimethylamino)-propylamino, 3-(dimethylamino)-2,2-(dimethyl)-propylamino, 4-(dimethylamino)-butylamino, aryl, heterocycloaryl, cycloalkyl, cycloalkenyl, heterocycloalkyl and heterocycloalkenyl.

6. A compound of claim 1, wherein Y is —O—, —S— or —NH.

7. A compound of claim 1, wherein Q is $C_1$-$C_{10}$ alkyl or $C_2$-$C_{10}$ alkenyl.

8. A compound of claim 1 wherein Z is $C_2$-$C_4$ alkenyl.

9. A compound of claim 1, wherein $R^1$ and $R^2$ are selected independently from each other from $C_1$-$C_{10}$ alkyl, $C_2$-$C_{10}$ alkenyl, $C_1$-$C_{10}$ heteroalkyl, haloalkyl, and alknyl.

10. A compound of claim 1, wherein X and Y are respectively attached to $C_5$ and $C_4$ position, or $C_4$ and $C_5$ position of the phenyl ring system.

11. A compound of claim 1, selected from: 3-(4-(2-(diethylamino)ethylthio)-3-(3-phenylpropylamino)phenyl)-N-hydroxy-Acrylamide, 3-(4-(2-(diethylamino)ethylthio)-3-(pentylamino)phenyl)-N-hydroxy-acrylamide, 3-(4-(2-(diethylamino)ethylthio)-3-(propylamino)phenyl)-N-hydroxy-acrylamide, 3-(3-acetamido-4-(2-(diethylamino)ethylthio)phenyl)-N-hydroxy-acrylamide, 3-(4-(2-(diethylamino)ethylthio)-3-nitrophenyl)-N-hydroxy-acrylamide, and 3-(3-(benzylamino)-4-(2-(diethylamino)ethylthio)phenyl)-N-hydroxy-acrylamide, or their pharmaceutically acceptable salts.

12. A pharmaceutical composition, comprising a compound according to claim 1 and a pharmaceutically acceptable carrier.

13. A method for treating a disease, comprising:

administering to a patient in need thereof a therapeutically effective amount of a compound of the formula (I):

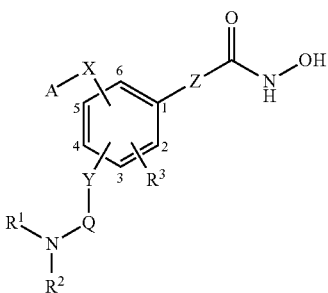

(I)

wherein,
A is selected from the group consisting of: H, —NO$_2$, —NH$_2$, alkyl, alkenyl, haloalkyl, haloalkenyl, heteroalkyl, alkoxy, alkoxyalkyl, alkenyloxy, alkynyloxy, alkylamino, aminoalkyl, alkylaminocarbonyl, sulfonyl, alkylsulfonyl, alkylsulfinyl, aminosulfonyl, acyl, arylalkyl, cycloalkylaryl, heteroaryl, and heterocycloalkyl, each of which is optionally substituted by one or more substituent selected from the group consisting of halogen, =O, —CF$_3$, alkyl, alkenyl, alkynyl, hydroxyl, hydroxyalkyl, alkoxy, alkoxyalkyl;

X is a covalent bond or a residual selected from the group consisting of methylene, —O—, —S—, —NH—, —NR$^7$—, —CO—NH—, —CO—NR$^7$—, —NH—CO—, —NR$^7$—CO—, —SO$_2$NH—, —NH—SO$_2$—, —NH—CO—NH—, —NH—CS—NH—, —CO—NH—CO—NH— and —CS—NH—CO—NH—; when X is —NH— or —NR$^7$—, A is neither aryl, heterocycloaryl, cycloalkenyl nor Heterocycloalkeny;

Y is selected from the group consisting of —O—, —S—, —NH— and —S(O)—;

X and Y are respectively attached to the phenyl ring position C$_3$, C$_4$ and or C$_5$;

Q is selected from a group consisting of —(CR$^8$R$^9$)n-, —(CR$^8$R$^9$)n-X—(CR$^{10}$R$^{11}$)m-, —Ar—X—(CR$^{10}$R$^{11}$)m-, —(CR$^8$R$^9$)n-X—Ar—, —Cy—X—(CR$^{10}$R$^{11}$)m- and —(CR$^8$R$^9$)n-X—Cy—;

n and m are independently 1, 2, 3, 4, 5 or 6;

Z is a C$_2$-C$_6$ alkenyl;

R$^1$ and R$^2$ are same or different and are selected independently from a group consisting of H, alkyl, alkenyl, haloalkyl, haloalkynyl, heteroalkyl, alkoxy, alkoxyalkyl, alkenoxy, alkynyloxy, amino, alkylamino, aminoalkyl, alkoxylcarbonyl, alkylaminocarbonyl, sulfonyl, alkylsulfonyl, alkylsulfinyl, aminosulfonyl and acyl, each of which is optionally substituted by one or more substituent selected from the group consisting of halogen, =O, =S, —CF$_3$, —OCF$_3$, alkyl, alkenyl, alkynyl, hydroxyl, hydroxyalkyl, alkoxy, alkoxyalkyl; alkenoxy, alkynyloxy, amino, alkylamino;

R$^3$ is selected from the group consisting of H, nitro, amino, alkyl and halogen;

R$^7$ is H, alkyl alkenyl, haloalkyl, haloalkenyl, cycloalkyl, heteroalkyl, hydroxyl, hydroxyalkyl, alkoxy, alkoxyalkyl, alkoxyaryl, alkenoxy, alkynoxy, cycloalkoxy, heterocycloalkoxy, amino, alkylamino, aminoalkyl, amide, COOH, alkoxycarbonyl, alkylaminocarbonyl, sulfonyl, alkylsulfonyl, alkylsulfinyl, aminosulfonyl, or acyl; each of which is optionally substituted by one or more substituent selected from halogen, =O, =S, —CN, —NO$_2$, —CF$_3$, —OCF$_3$, alkyl, alkenyl, alkynyl, haloalkyl, haloalkenyl, haloalkynyl, hydroxyl, hydroxy-alkyl, alkoxy, alkoxyalkyl, alkenoxy, alkynoxy, amino, alkylamino, sulfonyl, alkylsulfonyl, aminosulfonyl, —COOH, —C(O)OR$^4$, —COR$^5$, —SH, —SR$^6$, —OR$^6$ and acyl;

R$^5$, R$^6$, R$^8$, R$^9$, R$^{10}$ and R$^{11}$ are independently from each other selected from a group consisting of H, alkyl, alkenyl, haloalkyl, haloalkenyl, cycloalkyl, heteroalkyl, hydroxyl, hydroxyalkyl, alkoxy, alkoxyalkyl, alkoxyaryl, alkenoxy, alkynoxy, cycloalkoxy, heterocycloalkoxy, amino, alkylamino, aminoalkyl, amide, COOH, alkoxycarbonyl, alkylaminocarbonyl, sulfonyl, alkylsulfonyl, alkylsulfinyl, aminosulfonyl and acyl;

Ar is aryl or heteroaryl, each of which is optionally substituted by one or more substituent selected from halogen, —CF$_3$, alkyl, alkenyl, alkynyl, hydroxy, hydroxyalkyl, alkoxy or alkoxyalkyl;

Cy is cycloalkyl or heterocycloalkyl, each of which is optionally substituted by one or more substituent selected from halogen, =O, —CF$_3$, alkyl, alkenyl, alkynyl, hydroxy, hydroxyalkyl, alkoxy or alkoxyalkyl, or a pharmaceutically acceptable salt or prodrug thereof, wherein the disease is selected from the group consisting of: rheumatoid arthritis, allergic contact dermatitis, colorectal cancer, advanced colorectal adenocarcinoma, breast cancer, lung cancer, childhood leukemia, acute lymphocytic leukemia, acute myeloid leukemia, chronic lymphocytic leukemia, chronic myeloid leukemia, hairy cell leukemia, acute promyelocytic leukemia, plasma cell leukemia, ovarian cancer, prostate cancer, and pancreatic cancer.

14. The method of claim 13, wherein the disease is rheumatoid arthritis or allergic contact dermatitis.

15. The method of claim 13, wherein A is selected from a group consisting of alkyl, alkenyl, acyl, each of which is optionally substituted by one or more substituent selected from halogen, =O, —CF$_3$, alkyl, alkenyl, alkynyl, hydroxy, hydroxyalkyl, alkoxy and alkoxyalkyl.

16. The method of claim 13, wherein X is selected from a group consisting of: —NH—, —NR$^7$—, —CO—NH—, —CO—NR$^7$—, —NH—CO—, —NR$^7$—CO—, —SO$_2$NH—, —NH—SO$_2$—, —NH—CO—NH—, —NH—CS—NH—, —CO—NH—CO—NH—, and —CS—NH—CO—NH—; when X is —NH— or —NR$^7$, A is neither aryl, heteroaryl, cycloalkenyl, nor heterocycloalkenyl.

17. The method of claim 13, wherein X is —NH—, —CONH—, —NR$^7$—, or a covalent bond, wherein R$^7$ is selected from a group consisting of methyl, ethyl, 2-hydroxyethyl, propyl, 3,3-dimethylbutyl, butyl, pentyl, and allyl.

18. The method of claim 13, where A-X is selected from a group consisting of —NH$_2$, —NO$_2$, —F, —Cl, methylamino, propylamino, isopropylamino, n-butylamino, iso-butylamino, pentylamino, hexyllamino, 2-(diethylamino)-ethylamino, 3-hydroxypropylamino, 3-(methoxy)propylamino, 3-isopropoxypropylamino, 2,2-(dimethyl)-propylamino, 3-(dimethylamino)-propylamino, 3-(dimethylamino)-2,2-(dimethyl)-propylamino, 4-(dimethylamino)-butylamino, aryl, heterocycloaryl, cycloalkyl, cycloalkenyl, heterocycloalkyl and heterocycloalkenyl.

19. The method of claim 13, wherein Y is —O—, —S— or —NH.

20. The method of claim 13, wherein Q is C$_1$-C$_{10}$ alkyl or C$_2$-C$_{10}$ alkenyl.

21. The method of claim 13, wherein Z is C$_2$-C$_4$ alkenyl.

22. The method of claim 13, wherein R$^1$ and R$^2$ are selected independently from each other from C$_1$-C$_{10}$ alkyl, C$_2$-C$_{10}$ alkenyl, C$_1$-C$_{10}$ heteroalkyl, haloalkyl, and alknyl.

23. The method of claim 13, wherein X and Y are respectively attached to $C_5$ and $C_4$ position, or $C_4$ and $C_5$ position of the phenyl ring system.

24. The method of claim 13, selected from: 3-(4-(2-(diethylamino)ethylthio)-3-(3-phenylpropylamino)phenyl)-N-hydroxy-Acrylamide, 3-(4-(2-(diethylamino)ethylthio)-3-(pentylamino)phenyl)-N-hydroxy-acrylamide, 3-(4-(2-(diethylamino)ethylthio)-3-(propylamino)phenyl)-N-hydroxy-acrylamide, 3-(3-acetamido-4-(2-(diethylamino)ethylthio)phenyl)-N-hydroxy-acrylamide, 3-(4-(2-(diethylamino)ethylthio)-3-nitrophenyl)-N-hydroxy-acrylamide, and 3-(3-(benzylamino)-4-(2-(diethylamino)ethylthio)phenyl)-N-hydroxy-acrylamide, or their pharmaceutically acceptable salts.

* * * * *